US007214380B1

(12) United States Patent
DeKruyff et al.

(10) Patent No.: US 7,214,380 B1
(45) Date of Patent: May 8, 2007

(54) ADJUVANT THERAPY

(75) Inventors: Rosemarie H. DeKruyff, Stanford, CA (US); Dale T. Umetsu, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 778 days.

(21) Appl. No.: 09/561,089

(22) Filed: Apr. 28, 2000

Related U.S. Application Data

(62) Division of application No. 09/339,068, filed on Jun. 23, 1999, now Pat. No. 6,086,898.

(60) Provisional application No. 60/090,390, filed on Jun. 23, 1998.

(51) Int. Cl.
 *A61K 39/35* (2006.01)
 *A61K 39/02* (2006.01)
(52) U.S. Cl. .............................. 424/275.1; 424/184.1; 424/234.1
(58) Field of Classification Search ............ 425/184.1, 425/278.1
 See application file for complete search history.

(56) References Cited

U.S. PATENT DOCUMENTS

| 4,180,563 A | | 12/1979 | Fauve |
|---|---|---|---|
| 5,679,349 A | * | 10/1997 | Scheifinger et al. |
| 5,698,679 A | * | 12/1997 | Nemazee |
| 5,935,568 A | * | 8/1999 | Dow et al. |

FOREIGN PATENT DOCUMENTS

| WO | WO 98/16247 A | 4/1998 |
|---|---|---|
| WO | WO 00/06588 | 2/2000 |

OTHER PUBLICATIONS

Baldridge et al. Vaccine 15(4):395-401, 1997.*
Schwartz et al. Am J Physiol Lung Cell Mol Phys. 280:L771-L778, 2001.*
Bosquet, et al. (1991) "Differences in Clinical and Immunologic Reactivity of Patients Allergic to Grass Pollens and to Multiple-Pollen Species," *J. Aller. Clin. Immunol.* vol. 88(1):43-53.
Creticos, et al. (1992) "Immunotherapy With Allergens," *J.A.M.A.* vol. 268(20):2834-2839.
Creticos, et al. (1996) "Ragweed Immunotherapy in Adult Asthma," *N. Eng. J. Med.* vol. 334:501-506.
DeKruyff, et al. (1997) "Antigen-Driven but Not Lipopolysaccharide-Driven IL-12 Production in Macrophages Requires Triggering of CD40," *J. of Immunology* vol. 158:359-366.
Gavett, et al. (1995) "Interleukin12 Inhibitors Antigen-induced Airway Hyperresponsiveness, Inflammation, and Th2 Cytokine Expression in Mice," *J. Exp. Med.* vol. 182:1527-1536.
Hsieh, et al. (1993) "Devleopment of $T_H1$ $CD4^+$ T Cells through IL-12 Produced by *Listeria*- Induced Macrophages," *Science* vol. 260:547-549.

Hsu, et al. (1996) "Immunoprophylaxis of Allergen-Induced Immunoglobulin E Synthesis and Airway Hyperresponsiveness *in vivi* by Genetic Immunization," *Nature Medicine* vol. 2(5):540-544.
Kim, et al. (1997) "An Ovalbumin-IL-12 Fusion Protien is More Effective than Ovalbumin Plus Free Recombinant IL-12 in Inducing a T helper Cell Type 1-Dominated Immune Response and Inhibiting Antigen-Specific IgE Production," *J. of Immunology* vol. 158:4137-4144.
Kiniwa, et al. (1992) "Recombinant Interleukin-12 Suppresses the Synthesis of Immunoglobulin E by Interleukin-4 Stimulated Human Lymphocytes," *J. Clin. Invest.* vol. 90:262-266.
Marshall, et al. (1995) "IL-12 Inhibits the Production of IL-4 and IL-10 in Allergen-Specific Human $CD4^+$ T Lymphocytes," *J. of Immunology* vol. 155:111-117.
Miller, et al. (1996) "Protective Immunity to *Listeria Monocytogenes* Elicited by Immunization with Heat-Killed *Listeria* and IL-12," *Annals of the New York Acad. of Sci.* vol. 797:207-227.
Nelson, (1997) "Does Allergen Immunotherapy Have a Role in the Treatment of Bronchial Asthma?" *Allergy and Asthma Proc.* vol. 18:157-162.
Okamura, et al. (1995) "Cloning of a New Cytokine that Induces IFN-γ Production by T Cells," *Nature* vol. 378-88-91.
Secrist et al. (Dec. 1993), "Allergen Immunotherapy Decreases Interleukin 4 Production in $CD4^+$ T Cells from Allergic Individuals." *J. Exp. Med.*, vol. 178:2123-2130.
Söderlund, et al. (1997) "Allergen Induced Cytokine Profiles in Type I Allergic Individuals Before and After Immunotherapy," *Immunology Letters* vol. 57:177-181.
Tripp et al. (1994), "Neutralization of IL-12 Decrease Resistance to *Listeria* in SCID and C.B-17 Mice." *Journal of Immunology*, vol. 152:1883-1887.

(Continued)

*Primary Examiner*—G. R. Ewoldt
(74) *Attorney, Agent, or Firm*—Pamela J. Sherwood; Bozicevic, Field & Francis LLP

(57) ABSTRACT

Methods are provided for the treatment of allergic and other immune disorders associated with overproduction of Th2 type cytokines by antigen specific T cells. Immunotherapy with adjuvants, as provided in the present invention, greatly inhibits the development of airway hyperreactivity and airway inflammation. Such immunotherapy is shown to reverse ongoing airway disease, and convert allergic inflammatory responses into protective immune responses. Conditions of particular interest include allergic conditions associated with production of Th2 cytokines and/or IgE antibodies, asthma, allergic rhinitis, and anaphylactic reactions. The addition of adjuvant induces a Th1-type immune response and can redirect an established Th2-type response to a Th1-type response for the selected antigen. Preferably, antigen-specific IgE production is reduced without altering the intensity of the antigen-specific proliferative response. One particularly preferred adjuvant for use in accordance with the present invention is a *Listeria* adjuvant.

14 Claims, 13 Drawing Sheets

OTHER PUBLICATIONS

Weber, (1997) "Immunotherapy with Allergens," *J.A.M.A.* vol. 278:1881-1887.

Yoshimoto, et al. (1997) "Interleukin 18 Together with Interleukin 12 Inhibits IgE Production by Induction of Interferon-γ Production from Activated B Cells," *Proc. Natl. Acad. Sci. USA* vol. 94:3948-3953.

Yeung et al. (1998) "Heat-killed Listeria monocytogenes as an adjuvant converts established murine Th2-dominated immune responses into Th1-dominated responses." *Journal of Immunology,* vol. 161(8):4146-52.

US 6,008,200, 12/1999, Krieg (withdrawn)

* cited by examiner

ADJUVANT THERAPY

PRIORITY CLAIM

The present application is a divisional of U.S. patent application Ser. No. 09/339,068, filed Jun. 23, 1999 and now issued as U.S. Pat. No. 6,086,898; which claims priority to U.S. provisional application Ser. No. 60/090,390, filed Jun. 23, 1998, the entire contents of which are incorporated herein by reference.

GOVERNMENT SUPPORT

This work was supported at least in part by grants RO1AI24571 and RO1AI26322 from the National Institutes of Health. The United States Government may have certain rights in this invention.

BACKGROUND

Allergy or hypersensitivity of the immune system in its different forms affects more than 20% of the human population. Furthermore, man is a highly susceptible species to anaphylaxis. After sensitization with an allergen, a second exposure elicits constriction of the bronchioles, in some cases resulting in death from asphyxia. This allergic reaction is mediated by allergen-specific antibodies, mostly of the IgE class. The antibodies can be directed against a variety of antigens, such as molecules from pollen, fungi, food, house dust mite, hymenoptera venoms or animal danders. The aggregation of mast cell and basophil high-affinity IgE receptors by IgE and antigen causes the release of mediators and cytokines, including heparin, eosinophil and neutrophil chemotactic factors, leukotrienes and thromboxanes.

While our understanding of the inflammatory process in allergic reactions and asthma has improved remarkably over the past decade, our ability to control them remains modest. The prevalence of asthma in industrialized countries has increased by almost 80% since 1980. The specific causes for this increase in prevalence are not clear, but the rise in prevalence may be due in part to the absence of effective therapies that reverse the progression of, or cure, this disease. Currently available therapies, such as inhaled corticosteroids, antileukotrienes or 2-agonists, focus rather on symptom relief, reduction or neutralization of effector molecules and inflammatory mediators. This approach, while effective for acute disease and for relieving symptoms, however, has limited long term salutary effects, since the environmental factors that cause and precipitate asthma are not eliminated, and patients redevelop symptoms of asthma when these medications are discontinued.

The profile of cytokines produced by CD4$^+$ T cells during an immune response determines the nature of effector functions which develop and regulates the outcome of an immune response. Production of IL-2 and IFN— during Th1-dominated responses is associated with vigorous cell-mediated immunity, the induction of IgG2a and inhibition of IgE synthesis, and with resistance to intracellular pathogens. In contrast, the production of IL-4, IL-5 and IL-10 during Th2-dominated responses is associated with humoral immunity and protection from autoimmune pathology. Overproduction of Th2-cytokines by allergen-specific CD4$^+$ T cells can result in the development of allergic disease and asthma.

One approach to allergic diseases is immunotherapy. Immunotherapy has proven to be effective when used properly, and it is hoped that advances in immunologic intervention will further improve the efficacy. Modification of allergens, and the use of cytokines, may succeed in shutting down production of specific IgE and thus cure symptomatic allergies. Alternative approaches have attempted to use cytokines to shift the immune response. IL-12, a heterodimeric cytokine produced by macrophages and dendritic cells, is potent in driving the development of Th1 cytokine synthesis in naive and memory CD4$^+$ T cells. However, several in vivo studies have demonstrated that rIL-12 as an adjuvant, while enhancing IFN— synthesis, in some cases paradoxically also increases IL-4 and IL-10 synthesis in antigen primed CD4$^+$ T cells.

In contrast with drug therapy, immunotherapy could result in long-term, favorable alteration of the patient's immunologic status. Immunological changes that have been described after immunotherapy include an initial rise in specific serum IgE, followed by a fall, and a rise in specific IgG ("blocking antibody"). Immunotherapy leads to a reduction in mediator release from mast cells in vitro, alterations in lymphocyte subsets, and a downregulation of IL-4 production from T cells (Secrist et al. (1993) *J. Exp. Med.* 178: 2123–2130). Several studies have shown a reduction in inflammation and a decrease in bronchial hyper-responsiveness after immunotherapy.

This immunotherapy strategy, however, which might cure asthma and reduce its prevalence, is feasible only if potent therapies are developed that reverse ongoing airway hyper-reactivity and reverse the ongoing allergic inflammatory process, which plays a critical role in the pathogenesis of asthma (Martinez et al. (1995) *New Eng. J. Med.* 332: 133–8). Conventional allergen immunotherapy, while capable of reducing specific IL-4 production, requires multiple injections over several years time and is associated with frequent failure (Creticos (1992) *JAMA* 268:2834–9). Experimental methods described up to now, for example using IL-12 as adjuvant (Kim et al. (1997) *J. Immunol.* 158:4137–44), or immunization with plasmids containing the cDNA for allergens (Hsu et al. (1996) *Nature Medicine* 2:540–544), while effective in preventing the development of Th2-dominated immune response, have not been shown to reverse ongoing airway hyperreactivity.

Current therapy for asthma aims to suppress inflammation with inhaled corticosteroids, sodium cromoglycate, or nedocromil sodium, all of which interfere with the cellular and cytokine interactions by diverse mechanisms, but do not address the initiating event in allergic asthma. By altering the immune response to allergen, it may be possible to control the trigger of asthma, and of other allergic disorders.

Relevant Literature

*Listeria monocytogenes*, a gram positive, intracellular, facultative bacterium, elicits a strong classical cell-mediated immune response, characterized by the presence of potent antigen-specific CD8 killer cells. *Listeria* rapidly activates innate immunity and induces high levels of IL-12. This results in high IFN— production in NK cells and stimulates the induction of strongly polarized Th1 CD4 T cells, as discussed in Hsieh et al. (1993). *Science* 260:547–549. The immune response against *Listeria* is discussed in Fauve, U.S. Pat. No. 4,180,563; in DeKruyff et al. (1997) *J. Immunol.* 158:359–366; Miller et al. (1996) *Ann. N.Y. Acad. Sci.* 797:207–227; and others.

IL-12 and its biological activity is characterized in Okamura et al. (1995) *Nature* 378:88–91. The role of IL-12 in suppressing IgE synthesis is discussed in Kiniwa et al. (1992) *J. Clin. Invest.* 90:262–266. IL-12 inhibition of the production of IL-4 and IL-10 is disclosed in Marshall et al., (1995) *J. Immunol.* 155:111–117. The combined activity of IL-12 and IL-18 on IgE synthesis is disclosed by Yoshimoto et al. (1997) *Proc. Natl. Acad. Sci. USA*, 94:3948–3953.

Weber (1997) *JAMA* 278(22):1881–1887 reviews immunotherapy with allergens. Bousquet et al. (1991) *J. Aller. Clin. Immunol.* 99:43–53 provide evidence for immunotherapy efficacy. Soderlund et al. (1997) *Immunol Lett* 57:(1–3):177–181 discuss allergen induced cytokine profiles in type I allergic individuals before and after immunotherapy. Nelson (1997). *Allergy Asthma Proc* 18(3):157–162; and Creticos et al. (1996) *N Engl J Med* 334(8):501–506, review the efficacy of immunotherapy for asthma exacerbated by seasonal ragweed exposure. Gavett et al. (1995) *J. Exp. Med.* 182:1527–1536 disclose a role for IL-12 in asthma immunotherapy.

SUMMARY OF THE INVENTION

Methods are provided for the treatment of allergic and other immune disorders associated with overproduction of Th2 type cytokines by antigen specific T cells. The subject methods are useful in converting an established antigen specific Th2-type T cell response to a Th1 type immune response. Conditions of particular interest include allergic conditions associated with production of Th2 cytokines and/or IgE antibodies, asthma, allergic rhinitis, and anaphylactic reactions. Preferred inventive methods improve upon established immunotherapy protocols through the administration of an inventive adjuvant. The addition of adjuvant induces a Th1-type immune response and can redirect an established Th2-type response to a Th1-type response for the selected antigen. Preferably, antigen-specific IgE production is reduced without altering the intensity of the antigen-specific proliferative response. One particularly preferred adjuvant for use in accordance with the present invention is a *Listeria* adjuvant.

DESCRIPTION OF CERTAIN PREFERRED EMBODIMENTS OF THE INVENTION

Figure 1:
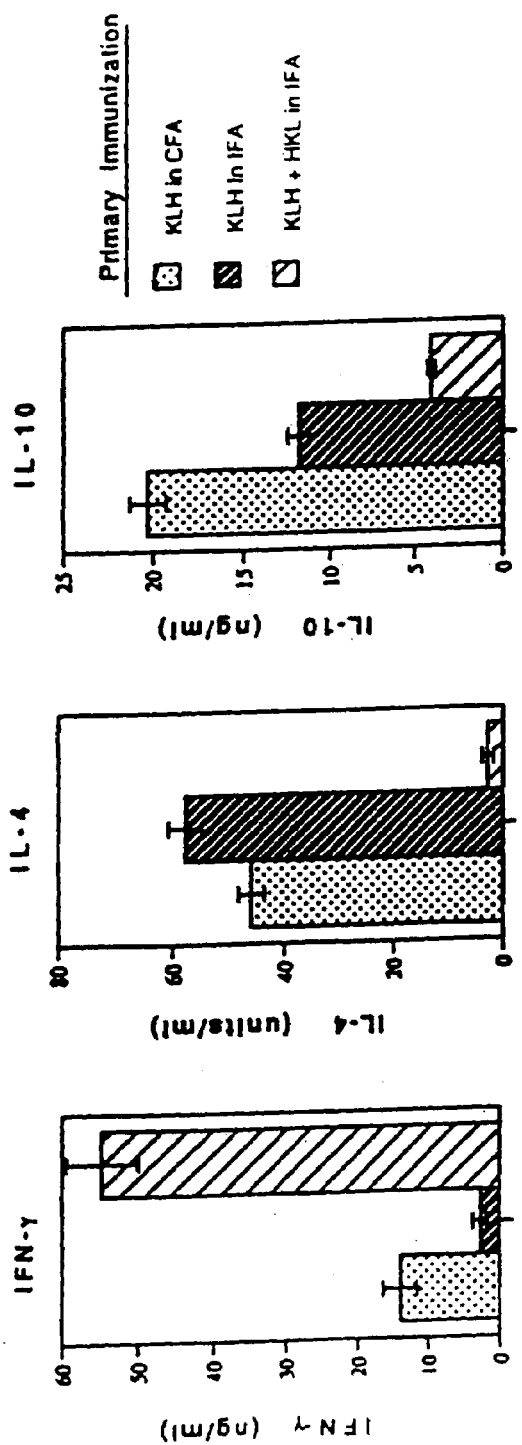
FIG. 1 shows that Heat killed *Listeria monocytogenes* (HKL) induces a strong Th1 dominated immune response when employed as an adjuvant.

The inventive methods and compositions provide a system for the treatment, prevention, and investigation of allergic responses, including asthma, through the induction of a specific, Th1-type T-cell response. After application of this system, the effects of the allergic response are decreased, which effects may include the synthesis of specific cytokines and IgE and/or physiological effects such as bronchial hyperreactivity, anaphylaxis, etc. In particular, the synthesis of allergen-specific IgE antibodies is decreased, thereby alleviating the symptoms of diseases such as asthma, allergic rhinitis, IgE-mediated anaphylactic reactions to allergens, and other allergic reactions.

One particularly useful application of the present invention is in the treatment, prevention, and investigation of asthma. Asthma is a respiratory disorder characterized by airway hyperreactivity and inflammation, and is associated with high serum IgE and overproduction of interleukin (IL)-4, IL-5, and IL-13 by allergen-specific T cells. As described in more detail below, the present invention demonstrates that heat killed *Listeria monocytogenes* (HKL) as an adjuvant in immunotherapy successfully reverses ongoing antigen-specific Th2-dominated responses, shifting the reaction to a Th1-type response. Furthermore, the present invention demonstrates that a single dose of antigen plus HKL as adjuvant significantly reduces airway hyperreactivity and reverses established airway hyperreactivity when given late after allergen sensitization. HKL as an adjuvant also dramatically decreases the effects of asthma associated allergies, including airway inflammation, eosinophilia and mucus production, significantly reduces antigen-specific IgE and IL-4 production, and dramatically increases IFN synthesis. HKL as an adjuvant for immunotherapy mediates immune deviation from a pathological Th2-dominated response towards a protective immune response in peripheral lymphoid tissues and in the lungs, and is effective in the treatment of patients with established asthma and allergic disease.

Another particularly useful application of the present invention is in the treatment, prevention, and investigation of anaphylactic allergic reactions. The inventive methods and reagents described herein may usefully be applied to any allergic reaction. However, the ability to induce Th1 responses, and/or to reverse Th2 responses to potentially anaphylactic antigens is particularly valuable in light of the risk of death posed by such antigens.

Definitions

As used herein, the singular forms "a", "and", and "the" include plural referents unless the context clearly dictates otherwise. Thus, for example, reference to "an immunization" includes a plurality of such immunizations, and reference to "the cell" includes reference to one or more cells and equivalents thereof, and so forth. All technical and scientific terms used herein have the same meaning as commonly understood by one of ordinary skill in the art to which this invention belongs unless clearly indicated otherwise. It should be understood that the terminology used herein is for the purpose of describing particular preferred embodiments of the invention only, and is not intended to limit the scope of the invention, which is defined only by the appended claims.

Adjuvants that are useful in accordance with the present invention are those that, when administered together with an antigen, induce a Th1-type response to that antigen and/or convert an established Th2-type response to that antigen to a Th1-type response. Preferred adjuvants induce Th1-associated cytokines (i.e., cytokines that induce and/or are produced during a Th1 response) such as IL-1, IL-2, IL-12, IL-18, IFN-α, IFN-γ, TFN-α etc. Preferred adjuvants also reduce levels of Th2-associated cytokines such as IL-4, IL-5, IL-10, etc.

A particularly preferred adjuvant is a *Listeria* adjuvant (see definition below). *Listeria* reduces IL-12 synthesis, making it a more effective adjuvant than IL-12 for reducing ongoing Th2-dominated immune responses. Furthermore, *Listeria* adjuvant effects may be localized to sites of antigenic stimulation, whereas the effects of IL-12, which diffuses rapidly into the systemic circulation, is more widespread than in the host, less antigen-specific, and appears to evoke sustained NK activation. Also, *Listeria* adjuvant may induce the production of several cytokines in addition to IL-12, such as IL-18, which is 10-fold more potent that IL-12 in inducing IFN, and which is also extremely effective in reducing IgE synthesis in B cells. Nonetheless, the present invention is not limited to the use of *Listeria* adjuvant. The present invention teaches that adjuvants known to induce Th1-type responses, but not Th2-type responses, may also be able to convert established Th2-type responses to Th1-type responses. Accordingly, any adjuvant known to stimulate Th1-type reactions and not Th2-type reactions may be analyzed as described herein for its ability to reverse Th2-type responses, and may be utilized in the inventive methods and compositions.

A large number of adjuvant compounds is known in the art; a useful compendium of many such compounds is prepared by the National Institutes of Health and can be found on the world wide web at http://www.niaid.nih.gov/daids/vaccine/pdf/compendium.pdf, incorporated herein by reference. See also Allison (1998) *Dev. Biol. Stand.* 92:3–11, Unkeless et al. (1988) *Annu. Rev. Immunol.* 6:251–281, and Phillips et al. (1992) *Vaccine* 10:151–158, each of which is incorporated herein by reference. Preferred useful adjuvants reported to induce Th1-type responses and not Th2-type responses include, for example, Aviridine® (N,N-dioctadecyl-N',N'-bis(2-hydroxyethyl)propanediamine) and CRL1005.

Preparations of microorganisms other than *Listeria* (e.g., bacille Calmette-Guerin [BCG], *Corynebacterium* species, *Mycobacterium* species, *Rhodococcus* species, Eubacteria species, *Bortadella* species, and *Nocardia* species) may also be tested for their ability to induce Th1 and not Th2 responses, and to reverse established Th2 responses, as described herein.

The dosage of adjuvant to be utilized in the practice of the present invention may vary depending on the condition of the patient, allergen, and particular adjuvant preparation that is administered. For example, for HKL adjuvant, the unit dosage for a single immunization may range from a dose equivalent to from about $10^5$ HKL per kilogram weight of the recipient to as much as about $10^9$ equivalents per kilogram weight.

*Listeria* adjuvant, as used herein, is intended to encompass any preparation of *Listeria monocytogenes* that induces a Th1-type immune response to an antigen administered together with the adjuvant and/or converts an established Th2-type reaction to that antigen into a Th1-type response. *Listeria* is a mildly infectious organism, so either live or killed preparations may be used in accordance with the present invention. Attenuated forms of *Listeria* are available that are preferred for use in live preparations (see, for example, Likhite, U.S. Pat. No. 4,816,253).

Preferred *Listeria* comprise killed *Listeria* or extracts or components thereof. Various methods of inactivating *Listeria*, including heat killing, killing by radiation, etc., are known in the art, as are extracts, fractions, or other components that maintain the adjuvant effect (i.e., the ability to induce a Th1 response and/or to convert a Th2 response to a Th1 response) of the complete killed bacteria. Particular components of interest, which may be prepared by any available means including purification from *Listeria* extracts, chemical synthesis, or production by expression in vivo or in vitro of a recombinant DNA construct, include, for example, listeriolysin O and p60. Other components of interest include lipoteichoic acid and *Listeria* nucleic acid including immunostimulatory CpG motifs.

A variety of different *Listeria* extracts that could be used in accordance with the present invention have been described in the literature. For example, cell wall and peptidoglycan fractions have been described by Paquet et al. (1991) *Infect. Immun.* 54(1):170–176; various cell wall preparations have been described by Hether et al. (1983) *Infect. Immun.* 39:111401121 and by Schuffler et al. (1976) *Immunology* 31(2):323–329. Other extracts may be prepared, or further purification of these extracts may be accomplished, using known separation and purification techniques such as, for example, affinity separation, preparative gel electrophoresis, HPLC, ion-exchange chromatography, etc.

Allergy, or Atopy is an increased tendency to IgE-based sensitivity resulting in production of specific IgE antibody to an immunogen including, for example, insect venom, dust mites, pollens, molds, animal dander, food antigens, or latex. Allergic responses are antigen specific and are characterized by the production of Th2-type cytokines such as, for example, IL-4, IL-5, IL-10, IL-13. Sensitization to a particular allergen occurs in genetically predisposed people after exposure to antigen; cigarette smoke and viral infections may assist in the sensitization process.

Included in the group of individuals suffering from atopy are those with asthma associated allergies. About 40% of the population is atopic, and about half of this group develops clinical disease ranging from trivial rhinitis to life-threatening asthma. After sensitization, continuing exposure to allergens leads to a significant increase in the prevalence of asthma. Ninety percent of children and 80% of adults with asthma are atopic. Once sensitization has occurred, re-exposure to allergen is a risk factor for exacerbation of asthma. Effective management of allergic asthma has typically required pharmacologic therapy and allergen avoidance. The specific physiological effects of asthma associated with allergies include airway inflammation, eosinophilia and mucus production, and production of IL-4 and antigen-specific IgE.

Both humans and non-human mammals suffer from allergic conditions. Fleas (*Ctenocephalides felis felis* and others)

are now recognized as a major cause of physiological disorders among mammals. These insects are ectoparasites that attack dogs, cats, and humans. Certain species (e.g., dogs and cats), and certain individuals within these species, are more allergic to flea bites than are others, resulting in a clinical disorder called flea allergy dermatitis (FAD) or flea bit hypersensitivity. The hallmark of FAD is intense pruritis (Itching) not only at the site of the flea bite but in a distinctive, body-wide distribution. This allergic reaction is a systemic response to a variety of protein substances in the oral secretions that the flea injects intradermally when it bites. Chronic FAD leads to scarring and permanent bald spots and is often associated with sebhorrea, giving the animal a foul odor that pervades the household. Flea allergy also is recognized as a contributory cause of the common dermatitis of man known as papular urticaria.

Allergens are immunogenic compounds that cause Th2-type T cell responses and IgE B cell responses in susceptible individuals. Allergens of interest according to the present invention include antigens found in foods such as fruits (e.g., melons, strawberries, pineapple and other tropical fruits), peanuts, peanut oil, other nuts, milk proteins, egg whites, shellfish, tomatoes, etc.; airborne antigens such as grass pollens, animal danders, house mite feces, etc.; drug antigens such as penicillins and related antibiotics, sulfa drugs, barbituates, anticonvulsants, insulin preparations (particularly from animal sources of insulin), local anesthetics (e.g., Novocain), and iodine (found in many X-ray contrast dyes); insect venoms and agents responsible for allergic dermatitis caused by blood sucking arthropods such as Diptera, including mosquitos (*Anopheles* sp., *Aedes* sp., *Culiseta* sp., *Culex* sp.), flies (*Phlebotomus* sp., *Culicoides* sp.) particularly black flies, deer flies and biting midges, ticks (*Dermmacenter* sp., *Ornithodoros* sp., *Otobius* sp.), fleas (e.g., the order Siphonaptera, including the genera *Xenopsylla*, *Pulex* and *Ctenocephalides felis felis*); and latex. The specific allergen may be any type of chemical compound such as, for example, a polysaccharide, a fatty acid moiety, a protein, etc. Antigen preparations may be prepared by any available technique including, for example, isolation from natural sources, in vivo or in vitro expression of recombinant DNA molecules (see, for example, Zeiler et al. (1997) *J. Allergy Clin. Immunol.* 100(6 Pt 1):721–727, chemical synthesis, or other technique known in the art.

A wide variety of antigen preparations are available in the art, and many antigens have been molecularly cloned. For example, cloned antigens include *Dermatophagoides pteryonyssinus* (Der P1); LoI pI-V from rye grass pollen; various insect venoms including venom from jumper ant *Myrmecia pilosula*, *Apis mellifera* bee venom phospholipase A2 (PLA$_2$) and antigen 5S, phospholipases from the yellow jacket *Vespula maculifrons* and white faced hornet *Dolichovespula maculata*; a large number of pollen proteins including birch pollen, ragweed pollen, *Parol* (the major allergen of *Parietaria oficinalis*) and the cross-reactive allergen *Parjl* (from *Parietaria judaica*) and other atmospheric pollens including *Olea europaea*, *Artemisia* sp., gramineae, etc.

Anaphylactic allergens are those antigens that pose a risk of anaphylactic reaction in hypersensitive individuals. Anaphylaxis is an acute, systemic allergic reaction that occurs after an individual has become sensitized to an antigen. Anaphylaxis is associated with the production of high levels of IgE antibodies and with the release of histamines, which cause muscle contractions, constriction of the airways, and dilation of blood vessels. Symptoms of anaphylactic reactions include hives, generalized itching, nasal congestion, wheezing, difficulty breathing, cough, cyanosis, lightheadedness, dizziness, confusion, slurred speech, rapid pulse, palpitations, nausea and vomiting, abdominal pain or cramping, skin redness or inflammation, nasal flaring, intercostal retractions, etc.

The most common anaphylactic allergens include food allergens (especially peanut allergens), insect venoms, drug allergens, and latex. Anaphylaxis is relatively rare in response to pollens and other inhaled allergens.

Test allergens are used to determine whether an individual is hypersensitive to a particular compound, and may be any antigen suspected of causing a hypersensitive immune response. Typically, an individual is subjected to test allergens in order to determine whether s/he is an appropriate candidate for allergen immunotherapy. A review of allergen tests currently in use is provided by Gordon (1998) *Otolaryngol. Clin. North Am.* 31(1):35–53. All current tests are capable of detecting allergic hypersensitivity, but the tests differ in their sensitivity, specificity, safety, reproducibility, and applications. Conventional tests for hypersensitivity include a skin test in which the allergen is injected intradermally. Contact with the allergen results in mast cell degranulation and release of histamines, heparin, eosinophil and neutrophil chemotactic factors, leukotrienes and thromboxanes, etc. A hypersensitive response typically will cause rapid production of a wheal and erythema within 30 minutes.

Allergen immunotherapy or hyposensitization involves administration of an antigen preparation to an individual under controlled circumstances, with the goal or reducing systems of hypersensitivity to the antigen and/or prevention of future anaphylactic reactions. Conventional approaches to allergen immunotherapy have involved parenteral administration of allergenic extracts at periodic intervals, usually on an increasing dosage scale (often distributed over a period of weeks) until a maintenance dose is achieved. Indications for immunotherapy are determined by appropriate diagnostic procedures coordinated with clinical judgment and knowledge of the patient history of allergic disease.

Immunotherapy is specific to the allergen being administered. Treatment results in a collection of immunologic changes, including: a shift in T cell response to the allergen from a Th2-type response to a Th1-type response, with corresponding changes in cytokine production, decreased allergen-specific IgE, increased allergen-specific IgG, decreased inflammatory cells, decreased mediators of inflammation, and/or decreased histamine-releasing factors. The intended result is decreased reactivity to the allergen in the target organ.

The amount of allergen preparation to be administered in inventive immunotherapy protocols may be empirically determined, and will depend, among other things, on the size of the recipient. Usually, at least about 100 ng of allergen will be required per kg of body weight, but more than 1 mg/allergen/kg body weight will usually not be desirable. Injection schedules may vary with individual patients, and may include periodic increases to the amount of allergen administered, optionally by as much as about ten to one hundred fold. To give but one example of a possible administration regimen, Allpyral preparations are administered every 1–2 weeks, with increasing doses until a maintenance dose is reached. Maintenance injections are administered every 2–4 weeks.

It should be emphasized that immunotherapy schedules are individualized and fixed schedules are not recommended, particularly when aqueous extracts are used. Even with conventional immunotherapy regimens, allergen injections rarely go on forever, but can usually be stopped after a patient has experienced no allergic symptoms and has required no medication for 18–24 consecutive months while on the maintenance schedule. Duration of treatment with conventional immunotherapy approaches is typically 3–5 years, but can be longer in certain clinical settings. If symptoms recur after a 6–12 months observation period following discontinuation of immunotherapy, re-evaluation is warranted.

In general, allergen immunotherapy is appropriate for at least the following indications: (i) severe, seasonal (lasting 2 or more years), or perennial, IgE-dependent allergic rhinoconjunctivitis in which optimal allergen avoidance and medication have not been sufficiently effective in controlling symptoms; (ii) IgE-mediated allergic asthma, particularly where (a) there is a clear temporal association between exposure to the allergen and signs and symptoms of asthma, and/or (b) symptoms have symptoms have occurred during two or more allergy seasons in successive-years; (iii) IgE-mediated asthma caused by house dust mites or ragweed pollen; (iv) history or occurrence of IgE-mediated anaphylactic reaction to an allergen (for example, immunotherapy with venom from yellow jackets, yellow hornets, white-faced hornets, wasps and honey-bees, and with whole body extracts of fire ants is effective); and (v) flea allergy dermatitis, particularly in pets such as cats and dogs.

Asthma, as defined herein, is reversible airflow limitation in an individual over a period of time. Asthma is characterized by the presence of cells such as eosinophils, mast cells, basophils, and $CD25^+$ T lymphocytes in the airway walls. There is a close interaction between these cells, because of the activity of cytokines which have a variety of communication and biological effector properties. Chemokines attract cells to the site of inflammation and cytokines activate them, resulting in inflammation and damage to the mucosa. With chronicity of the process, secondary changes occur, such as thickening of basement membranes and fibrosis. The disease is characterized by increased airway hyperresponsiveness to a variety of stimuli, and airway inflammation. A patient diagnosed as asthmatic will generally have multiple indications over time, including wheezing, asthmatic attacks, and a positive response to methacholine challenge, i.e., a PC20 on methacholine challenge of less than about 4 mg/ml. Guidelines for diagnosis may be found, for example, in the *National Asthma Education Program Expert Panel Guidelines for Diagnosis and Management of Asthma*, National Institutes of Health, 1991, Pub. No. 91–3042.

Methods of Immunotherapy

The present invention provides improved immunotherapeutic methods, in which an antigen is administered to a subject wishing to be desensitized to the antigen in combination with an inventive adjuvant. The inventive approach elicits a Th1-type immune response that is specific for the particular antigen. Moreover, where there is an established Th2-type response to that antigen, the inventive methods result in a conversion of the cytokine profile to a Th1 profile.

The present inventive methods involve administration of both an antigen and an adjuvant to an individual who is to be desensitized to the antigen. The adjuvant and allergen can be delivered simultaneously, or within a short period of time, by the same or by different routes. In one embodiment of the invention, the adjuvant and allergen are co-formulated, meaning that they are delivered together as part of a single composition. The antigen and adjuvant may be associated with one another by covalent linkage, or by non-covalent interaction such as hydrophobic interaction, hydrogen bonding, ionic interaction, van der Waals interaction, magnetic interaction, or combinations thereof. Alternatively, the antigen and adjuvant may simply be mixed in a common suspension. Also, the adjuvant and antigen may be encapsulated together in some form of delivery device such as, for example, an alginate device, a liposome, chitosan vesicle, etc. (see, for example, WO 98/33520, incorporated herein by reference).

The adjuvant and allergen may be delivered by any available route. Moreover, different portions of the total dose of antigen and/or adjuvant may be administered by different routes. In some embodiments, systemic administration will be preferred, in others local administration may be sufficient. Acceptable modes of administration include but are not limited to inhalation (e.g., by means of a pulmonary aerosol), intranasal administration, oral administration, injection (e.g., subcutaneously, intramuscularly, etc.), transdermal administration, vaginal administration, rectal administration, ocular administration, etc.

The immunization protocol may be repeated for extended periods of time, and may include escalations or reductions in adjuvant and/or allergen doses. Treatment will generally be continued until there is a substantial reduction in hyperreactivity and/or a detectable induction of a protective Th1-type response. For example, a 50% decrease in the serum concentration of allergen-specific IgE (for example measured according to standard techniques such as ELISA, RIA, etc.), decreased bronchial hyperreactivity (for example measures by methacholine challenge), decreases in Th2-associated cytokines, and/or increases in Th1-associated cytokines can be used as end-points of successful treatment.

Any formulation of allergen may be used in accordance with the present invention. The antigen may be in a "natural" form in that no human intervention was involved in preparing the antigen or inducing it to enter the environment in which it encounters the APC. Alternatively or additionally, the antigen may comprise a crude preparation, for example of the type that is commonly administered in a conventional allergy shot. The antigen may alternatively be substantially purified, preferably being at least about 90% pure.

Where the antigen is a polypeptide or protein antigen, provision of the antigen may comprise provision of a gene encoding the antigen, so that expression of the gene results in antigen production either in the individual being treated or in another expression system (e.g., and in vitro transcription/translation system or a host cell) from which expressed antigen can be obtained for administration to the individual. Techniques for generating nucleic acids including an expressible gene, and for introducing such nucleic acids into an expression system in which any protein encoded by the expressible gene will be produced, are well established in the art (see, for example, Sambrook et al., *Molecular Cloning: A Laboratory Manual,* 2nd Ed., Cold Spring Harbor Laboratory Press, Cold Spring Harbor, N.Y., 1989, incorporated herein by reference). These same techniques allow the ready production of fusion proteins, in which portions of sequence from a first polypeptide (e.g., a first antigen) are covalently linked to portions of sequence from a second polypeptide (e.g., a second antigen, a signal sequence, a transmembrane domain, a purification handle, etc.) by means of a peptide bond. Those of ordinary skill in the art will appreciate the diversity of such fusion proteins for use in accordance with the present invention. Recombinant techniques further allow for the ready modification of the amino acid sequence of polypeptide or protein antigens, by substitution, deletion, addition, or inversion of amino acid sequences.

Where the antigen is a peptide, it may be generated, for example, by proteolytic cleavage of isolated proteins. Any of a variety of cleavage agents may be utilized including, but not limited to, pepsin, cyanogen bromide, trypsin, chymotrypsin, etc. Alternatively, peptides may be chemically synthesized, preferably on an automated synthesizer such as is available in the art (see, for example, Stewart et al., *Solid Phase Peptide Synthesis*, 2d. Ed., Pierce Chemical Co., 1984; see also Example 2). Also, recombinant techniques may be employed to create a nucleic acid encoding the peptide of interest, and to express that peptide under desired conditions (e.g., in a host cell or an in vitro expression system from which it can readily be purified).

The antigen employed in accordance with the present invention may be a naturally-occurring compound or may alternatively have a structure that is distinct from any naturally-occurring compound. In certain embodiments of the invention, the antigen is a "modified antigen" in that the antigen has a structure that is substantially identical to that of a naturally-occurring antigen but that includes one or more deviations from the precise structure of the naturally-occurring compound.

For instance, where the naturally-occurring antigen is a protein or polypeptide antigen, a modified antigen as compared with that protein or polypeptide antigen would have an amino acid sequence that differs from that of the naturally-occurring antigen in the addition, substitution, or deletion of one or more amino acids, and/or would include one or more amino acids that differ from the corresponding amino acid in the naturally-occurring antigen by the addition, substitution, or deletion of one or more chemical moieties covalently linked to the amino acid. Preferably, the naturally-occurring and modified antigens share at least one region of at least 5 amino acids that are at least approximately 75% identical. Those of ordinary skill in the art will appreciate that, in comparing two amino acid sequences to determine the extent of their identity, the spacing between stretches (i.e., regions of at least two) of identical amino acids need not always be precisely preserved. It is generally preferred that naturally-occurring and modified protein or polypeptide antigens show at least approximately 80% identity, more preferably 85%, 90%, 95%, or greater than 99% identity in amino acid sequence for at least one region of at least 5 amino acids. Often, it will be preferable for a much longer region (e.g., 10, 20, 50, or 100 or more amino acids) of amino acid sequence to show the designated degree of identity.

Common allergens may be administered at dosages known in the art. For example, venom antigens may be provided in graded doses ranging from about 0.01 μg of venom to about 100 μg of venom; allergens such as penicillin may be administered in doses ranging from about 0.001 μg to about 250 mg.

As mentioned above, allergen may be administered separately from or together with adjuvant. More than one allergen, and/or more than one adjuvant may be employed. Either or both of the allergen and adjuvant may be administered with other pharmaceutically active compounds. For example, one or both of the allergen and adjuvant may be administered with immune modulators such as IL-12, IL-18, etc. Preferably, the immune modulators are present in a dosage sufficient to enhance the effectiveness of the inventive adjuvant. Allergen and/or adjuvant may be formulated with Freund's incomplete adjuvant, with QS21, or with others. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacial, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters or higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant is placed in proximity to the site of response, where applicable, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host. Unit dosage forms for injection or intravenous administration may comprise the compound of the present invention in a composition as a soluble in sterile water, normal saline or another pharmaceutically acceptable carrier.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 ug to 100 milligrams per kg weight of subject per administration. A typical dosage may be one sub-cutaneous injection administered at weekly or semi-weekly intervals. A time-release effect may be obtained by capsule materials that dissolve at different pH values, by capsules that release slowly by osmotic pressure, or by any other known means of controlled release.

Those of skill in the art will readily appreciate that dose levels can vary as a function of the specific allergen, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Mammalian species susceptible to allergic conditions include canines and felines; equines; bovines; ovines; etc. and primates, particularly humans. Animal models, particularly small mammals, e.g. murine, lagomorpha, etc. may be used for experimental investigations. Animal models of interest include those involved with the production of antibodies having isotypes associated with IL-12, or IL-18 production. Other uses include investigations where it is desirable to investigate a specific effect in the absence of T cell mediated allergic reactions.

EXAMPLES

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

Example 1

Conversion of Cytokine Profiles Using *L. monocytogenes* as an Adjuvant

*Listeria monocytogenes* is used as an adjuvant to generate a specific immune response characterized by high antigen-specific IFN-γ production, and large quantities of specific IgG2a antibody. Moreover, vaccination with heat killed *Listeria* and antigen during an established Th2 dominated, antigen-specific immune response resulted in significant reductions in IL-4 and IL-10 synthesis, increases in IFN-γ production, and reduction in antigen-specific IgE. Reduction in IL-4 and IL-10 synthesis did not reduce the intensity of the antigen-specific immune response, since T cell proliferation to the antigen was not reduced. Neutralization of IL-12 activity with anti-IL-12 mAb at the time of boosting with antigen blocked reduction of IL-4 and enhancement of IFN-γ production, indicating that HKL-induced IL-12 was responsible for the adjuvant effects on cytokine production. This technique may be useful in clinical situations to induce appropriate cytokine synthesis during vaccination and in treatment of ongoing diseases caused by heightened Th2 cytokine responses.

Materials and Methods

Animals BALB/cByJ mice were obtained from the Jackson Laboratory, Bar Harbor, Me. Animal protocols used in this study were approved by the Stanford University Committee on Animal Welfare.

Antigens. Keyhole Limpet Haemocyanin (KLH) was obtained from Calbiochem, San Diego, Calif.

Immunizations. BALB/c mice were immunized in the footpads with KLH (100 µg/mouse) emulsified in complete Freund's adjuvant (CFA), or in incomplete Freund's adjuvant (IFA) with or without heat-killed *Listeria monocytogenes* (HKL, $10^8$ bacteria/mouse). CFA contains the same oil base as does IFA, but CFA also contains killed mycobacteria. In some experiments BALB/c mice were first primed in the footpads, with KLH (10 µg) adsorbed to 2 mg of alum (Al[OH]$_3$), a priming method that invokes a strong Th2 response. Four weeks later mice were treated with KLH (100 µg) in CFA, or in IFA with or without HKL ($10^8$ bacteria). After an additional 10 days all mice received another dose of KLH (100 µg) in PBS.

Monoclonal Antibodies. Anti-IFN-γ mAb R46A2 (HB170, ATCC), and anti-IL-4 mAb (11B11), were prepared from serum-free culture supernatants by ammonium sulfate precipitation. Monoclonal anti-IL-2 antibody S4B6 and anti-IFN-γ antibody XMG1.2 were obtained from Dr. Tim Mosmann (Univ. of Alberta, Edmonton, Canada). Anti-IL-4 mAb BVD4-1D11 and BVD6-24G2 were obtained from DNAX Research Institute, Palo Alto, Calif. Each of these antibodies was purified from ascites by ammonium sulfate precipitation and ion-exchange chromatography. Anti-IL-10 mAb SXC.1 (DNAX) was purified by ammonium sulfate precipitation followed by Sepharose 4B chromatography. Anti-IL-10 mAb 2A5 was purchased from Pharmingen (San Diego, Calif.). Neutralizing anti-IL-12 mAb C17.8 was purified from ascites by affinity chromatography. Anti-IL-12 mAb C15.6.8, which recognizes an independent epitope of the IL-12 p40 chain, was purified from ascites by affinity chromatography. Anti-38C13 iditoype mAb4G10 (rat IgG2a) (Maloney et al. (1985) *Hybridoma*. 4: 191–209) was used as isotype control.

Treatment of mice with anti-cytokine antibodies BALB/c mice were injected i.p. with 1 mg of mAb C17.8 (for IL-12 depletion), XMG1.2 (for IFN-γ depletion) or 4G10 (rat IgG2a control) in 0.5 ml PBS one day before, the day of, and 3 days following immunization with KLH in IFA or KLH in IFA with HKL.

Medium Cells were cultured in DMEM (Life Technologies, Grand Island, N.Y.), which was supplemented as previously described (Clayberger et al. (1983) *J. Exp. Med.* 157: 1906–19), and contained $5 \times 10^{-5}$ M 2-mercaptoethanol and 10% Fetal Bovine Serum (HyClone Laboratories, Logan, Utah).

Restimulation of lymph node cells in vitro. Draining lymph nodes were removed 7 days after priming or booster immunization, depleted of resting B cells by adherence to goat anti-mouse Ig-coated plates, and $4 \times 10^5$ cells were restimulated in vitro with KLH. Cultures were set up in 96 well microtiter plates in 150 µl medium. Supernatants were harvested after four and five days for determination of IL-4, IL-10, and IFN-γ levels. Cytokine levels for each sample were measured in triplicate by ELISA. Proliferation was assessed by pulsing cultures overnight with [$^3$H]-thymidine after 36 hours of culture.

Cytokine ELISA 96-well plates were coated overnight with primary anti-cytokine capture antibody. Plates were washed, blocked, and dilutions of supernatants or standards were added. Dilutions of culture supernatants were incubated overnight at 4° C., and after washing, the wells were incubated with biotin conjugated anti-cytokine-detecting mAb. After a two hour incubation the plates were washed and an HRP-streptavidin conjugate (Southern Biotechnology Associates, Inc., Birmingham, Ala.) was added. The plates were incubated for an additional hour and after washing OPD substrate was added. After developing, the OD was determined at 492 nm. The amount of cytokine in each supernatant was extrapolated from the standard curve. The antibody pairs used were as follows, listed by capture/biotinylated detection: IFN-γ, R4-6A2/XMG1.2; IL-12, C17.8/C15.6; IL-10, 2A5/SXC.1; IL-4, 11B11/BVD6-24G2. The standards were recombinant cytokine curves generated in 1:2 dilutions from 20–0.156 ng/ml for IFN-γ, 4,000 to 30 pg/ml for IL-12, 20–0.1 ng/ml for IL-10 and 10 to 0.15 units/ml for IL-4. One unit of IL-4 is equivalent to 50 picograms.

Measurement of anti-KLH antibody isotypes Mice were bled at the time of sacrifice and KLH-specific antibody was measured using a modified antigen-specific ELISA. For measurement of KLH specific IgG1 and IgG2a, plates were coated overnight with 2 µg/ml KLH. After washing and blocking, serial diluted sera were added to the plates. Following overnight incubation, the plates were developed using HRP-conjugated goat anti-IgG subclass-specific antibodies (Southern Biotechnology Associates, Birmingham, Ala.). After additional washing, OPD substrate was added, the plates developed and the OD determined at 492 nm. The concentration of anti-KLH antibody was estimated using standard curves constructed by coating wells with 1 µg/ml goat anti-mouse IgG1 or anti-IgG2a (Southern Biotechnology Associates) and adding polyclonal mouse Ig standards of the pertinent subclass. Determination of KLH-specific IgE was performed by ELISA, using rat anti-mouse IgE mAb EM95 (0.5 µg/ml) to coat plates. After the samples were applied and incubated overnight, plates were washed and biotinylated-KLH (5 µg/ml) was added. Three hours later, plates were washed and HRP-conjugated streptavidin (Southern Biotechnology Associates) was added. Plates were developed with O-phenyl-diamine substrate and the OD determined at 492 nm.

Preparation of heat-killed *L. monocytogenes* A clinical isolate of *L. monocytogenes* was provided by Dr. Lucy Tompkins and Barbara Allen, Stanford University. A heat killed preparation of bacteria (HKL) was prepared by growing nutrient broth cultures (Difco, Detroit, Mich.) overnight at 37° C. on a rotator. Cultures in log phase growth were harvested, centrifuged, and washed three times in PBS. The recovered bacteria were resuspended in PBS and incubated at 80° C. for one hour. After two additional washes in PBS, absence of viable colonies was confirmed by lack of growth on nutrient agar plates. Bacteria concentration was enumerated by comparing the absorbance of a serial dilution of HKL at 570 nm compared with a standard dilution of a known concentration of *Listeria* previously enumerated by counting the outgrowth of colonies from serial dilutions of bacteria plated on nutrient agar. The HKL was kept at −80° C.

Results

Heat-Killed *Listeria* as adjuvant at the time of antigen priming enhances IFN-γ but inhibits IL-4 and IL-10 production. The ability of heat killed *Listeria monocytogenes* (HKL) to act as a Th-1-inducing adjuvant in vivo was investigated. The HKL activates a potent innate immune response characterized by the induction of IL-12, which induces rapid production of IFN-γ, but inhibits the synthesis of IL-4, in NK cells and CD4$^+$ T cells. For these experiments, we immunized BALB/c mice subcutaneously with KLH (100 µg) plus HKL (10$^8$ bacteria) in incomplete Freund's adjuvant (IFA). Control mice received KLH in IFA or in complete Freund's adjuvant (CFA). Seven days after immunization, draining lymph nodes (LN) were removed, and LN cells were restimulated with KLH in vitro. LN cells (4×10$^5$) were cultured with KLH (10 µg/ml). Supernatants were harvested after 96 hours. IL-4, IL-10, and IFN-γ levels were determined by ELISA. Cytokine production in the absence of antigen was very low (IFN-γ<0.8 ng/ml, IL-4<0.25 unit/ml, IL-10<200 pg/ml). Data are the mean of triplicate cytokine determinations±SEM. Representative results from one of three experiments are presented. FIG. 1 shows that HKL induced the development of lymph node cells with a strongly biased Th1-like cytokine pattern, characterized by production of large quantities of IFN-γ and very low levels of IL-4.

The level of IFN-γ was significantly greater and the levels of IL-4 were significantly lower than the quantities produced by LN cells from mice that had received KLH in IFA or that had received KLH in CFA. Furthermore, the cells from mice immunized with KLH+HKL produced much lower quantities of IL-10, demonstrating the shift from a Th2-like cytokine profile. These data indicate the HKL is a potent Th1 cytokine inducing adjuvant in vivo.

Figure 2:
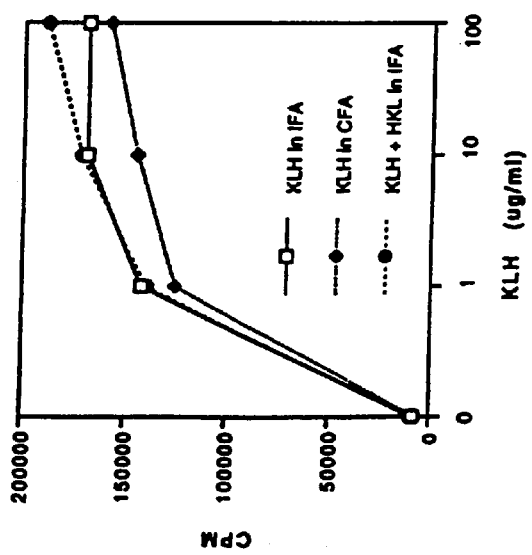
FIG. 2 shows that HKL as adjuvant does not alter the magnitude of the proliferative response to KLH.

Although the cytokine profiles of LN cells from the three groups of mice differed significantly, the magnitude of the proliferative response was similar regardless of the priming condition used (FIG. 2). LN cells from mice primed with KLH in IFA, KLH in CFA or KLH+HKL in IFA all prolifereated to the same extent when stimulated with a wide range of antigen concentrations. LN cells (4×10$^5$) were cultured with KLH at the indicated concentration. Proliferation was determined by addition of 1 µCi [$^3$H]-thymidine 72 hours after the initiation of culture. Representative results from one of three experiments are presented. Thus addition of HKL as adjuvant to KLH did not alter the intensity of the KLH specific immune response. The similar dose dependent proliferation between groups primed under different conditions, and the lack of significant cytokine production in the absence of antigen indicated that priming with HKL has minimal effect on the specificity of the response to KLH.

Administration of Heat-killed *Listeria* during secondary antigen challenge. We next examined the capacity of HKL to enhance Th1 cytokine synthesis in established Th2-cytokine dominated immune responses. In these experiments, BALB/c mice were first primed with KLH (10 µg/mouse) adsorbed to alum (2 mg/mouse), which is known to provoke antigen-specific Th2-dominated immune responses. Four weeks later, mice were immunized subcutaneously with KLH (100 µg/mouse) plus 10$^8$ HKL in IFA, or with KLH in CFA or KLH in IFA. After an additional 10 days, all mice received a subcutaneous booster immunization of KLH (100 µg) in no adjuvant, to mimic persistent, though non-biasing, in vivo antigenic stimulation. The draining lymph nodes were removed 7 days later and the cells were cultured in vitro with KLH.

Figure 3:
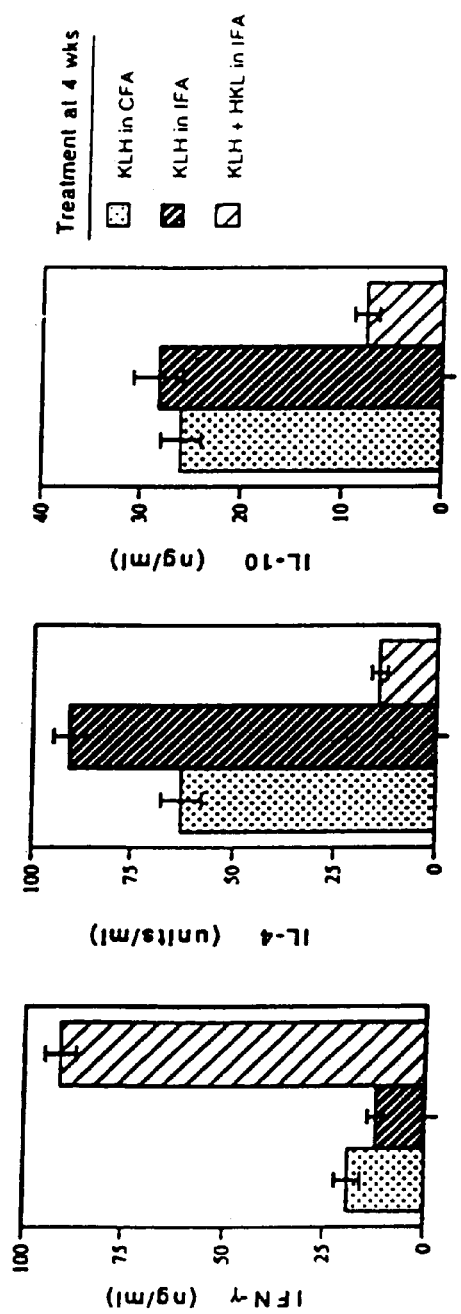
FIG. 3 shows the conversion of established Th2-to Th1-like cytokine responses by use of HKL as an adjuvant.

FIG. 3 shows that HKL as an adjuvant was extremely effective in enhancing IFN-γ and in reducing IL-4 and IL-10 synthesis in the draining LN cells compared to controls. BALB/c mice were primed in the footpads with KLH (10 µg) adsorbed to 2 mg alum. Four weeks later mice were injected subcutaneously with KLH (100 µg/mouse) in IFA or in CFA, or with KLH plus 10$^8$ HKL in IFA. After an additional 10 days, all mice received a subcutaneously booster immunization of KLH (100 µg) in no adjuvant. The draining lymph nodes were removed 7 days later and the cells were cultured in vitro with KLH (0 or 10 µg/ml) at 5×10$^5$ cells/well. IL-4, IL-10 and IFN-γ levels in supernatants were determined after four days by ELISA. Cytokine production in the absence of antigen was negligible (IL-4 <0.5 units/ml, IL-10 <200 pg/ml, IL-12<60 pg/ml, IFN-γ<1.0 ng/ml). Data are the mean of triplicate cytokine determinations SEM. Representative results from one of five experiments are presented. There was a slight reduction in IL-4 production in mice receiving CFA as adjuvant compared to mice receiving IFA as adjuvant, but the reduction in IL-4 production was much greater in mice receiving HKL as adjuvant. In addition, HKL was much more effective than CFA in reducing IL-10 synthesis. Finally, the proliferative responses in all groups were similar, with negligible proliferation in the absence of in vitro antigen. Together, these data demonstrate the HKL can act as a potent Th1 cytokine inducing adjuvant, and also reduce preexisting Th2 cytokine production in an antigen-specific manner.

The effect of HKL on IL-4 and IFN-γ production is mediated by IL-12. Since HKL is a potent inducer of IL-12 production, and since IL-12 is known to inhibit production of IL-4 and enhance production of IFN-γ, we asked if the effects of HKL as adjuvant on cytokine production were mediated primarily by IL-12. Mice were first primed with KLH in alum to induce a Th2-dominated immune response. As in the experiments shown in FIG. 3, the mice were vaccinated with KLH plus HKL in IFA or KLH in IFA. Some mice received three i.p. injections of the anti-IL-12 mAb C17.8: one dose just prior to boosting with KLH+HKL (four weeks after priming), another dose on the day of boosting, and the final dose three days after boosting.

Figure 4A:
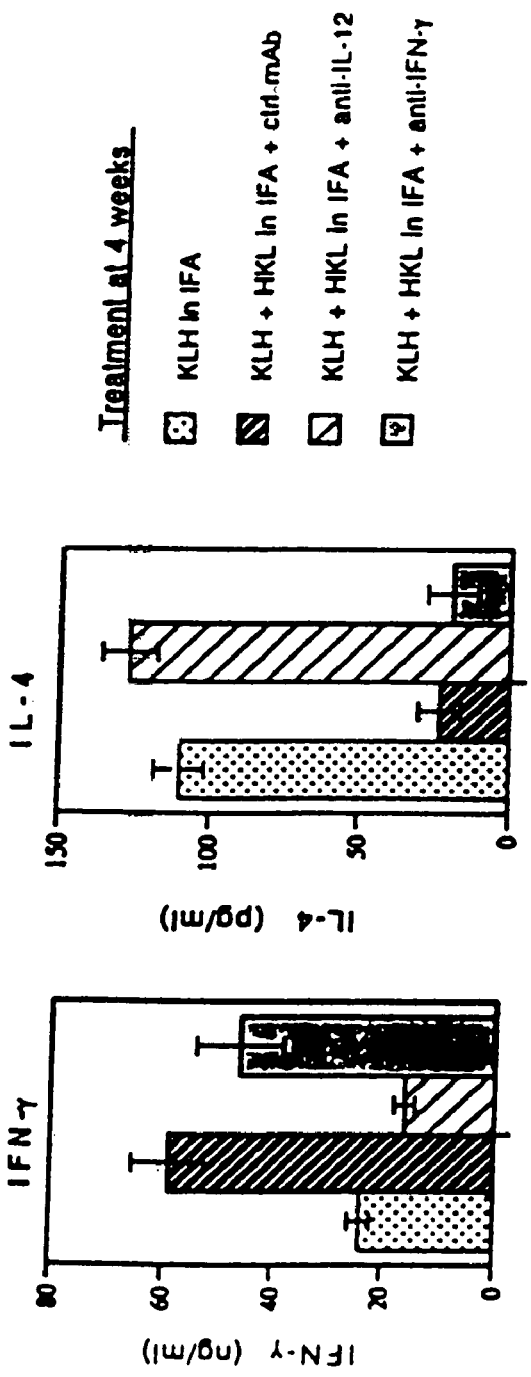
FIGS. 4A and 4B show that administration of anti-IL-12 mAb blocks the effect HKL adjuvant on cytokine production.

FIG. 4A shows that the treatment of the KLH primed mice with KLH plus HKL, as expected, greatly enhanced IFN-γ production and greatly reduced IL-4 production in LN cells taken from these mice. Mice were treated as noted in FIG. 3. Four weeks after the initial priming with KLH in alum, mice were injected subcutaneously with KLH (100 μg/mouse) in IFA, or with KLH plus $10^8$ HKL in IFA. As indicated, BALB/c mice were injected i.p. with mAb (1 mg/dose) C17.8 (for IL-12 depletion), XMG1.2 (for IFN-γ depletion) or 4G10 (rat IgG2a control) in 0.5 ml PBS one day before, the day of, and 3 days following the immunization with KLH+HKL. After an additional 10 days all mice received a 100 μg booster immunization of KLH in PBS. Seven days later lymph node cells were removed and cultured ($5 \times 10^5$ cells/well) with KLH (1 μg/ml). The values represent the mean±SD of triplicate determinations. Panels A and B show results from two of four experiments.

Neutralization of IL-12 in such mice with anti-IL-12 mAb reversed the enhanced IFN-γ production and the reduction in IL-4 production, indicating that IL-12 mediated much of the in vivo effects of HKL on cytokine production. Although IL-12 was critical for enhanced IFN-γ and reduced IL-4 production, the presence of IFN-γ was not important in regulating cytokine synthesis by HKL, since neutralization in vivo of IFN-γ with an anti-IFN-γ mAb XMG1.2 had minimal effect on ex vivo IFN-γ and IL-4 synthesis (FIG. 4A). The effects of HKL on Th2 cytokine production involved other factors in addition to IL-12, since the reduction in IL-10 production by HKL was not reversed by treatment with anti-IL-12 mAb. These findings indicate that the effects of HKL as an adjuvant on IL-4 and IFN-γ production are mediated by IL-12 and not by the enhanced levels of IFN-γ, but that IL-12 independent mechanisms are also implicated, particularly in reducing IL-10 synthesis.

Figure 4B:
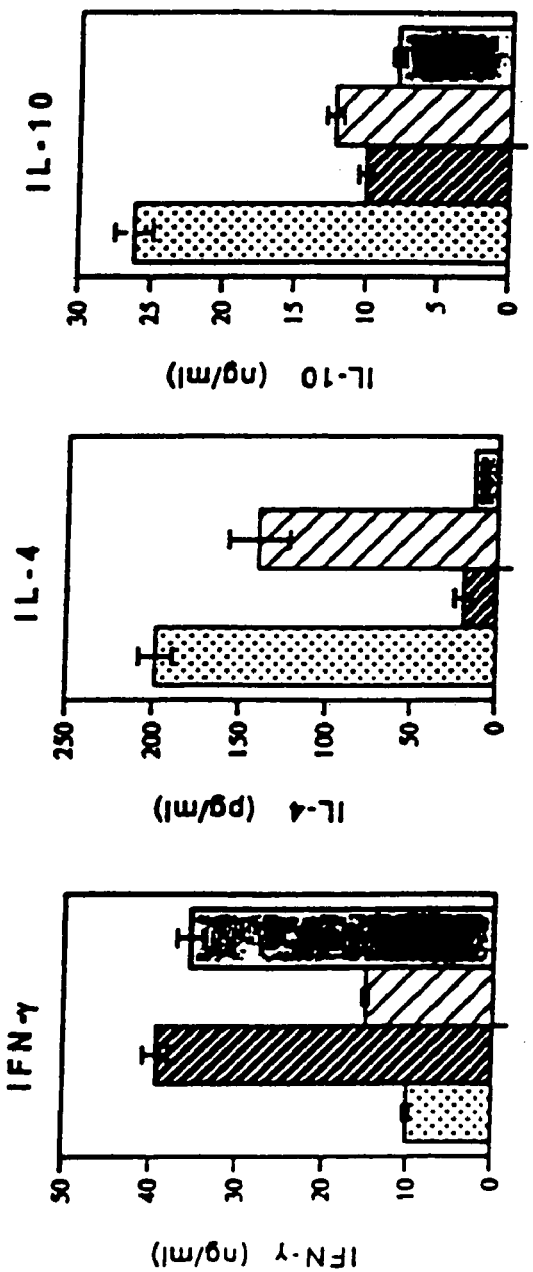

Immunization with HKL as adjuvant promotes the production of KLH-specific IgG2a and inhibits KLH-specific IgE synthesis. We next asked if the isotype and subclass distribution of anti-KLH antibody were altered by treatment with HKL. Mice were first primed with KLH in alum to generate a Th2 dominated immune response, and then treated with KLH plus HKL. After an additional boost with antigen at 5.5 wks (same protocol as in FIGS. 3 and 4), serum was collected and KLH-specific antibody responses were determined by isotype- and IgG subclass specific ELISA. Mice treated with KLH plus HKL showed enhanced anti-KLH IgG2a antibody responses (2.5 to 2.8-fold enhancement in three experiments), and reduced anti-KLH IgE responses (59.6% to 79.6% reduction in four expts) as compared with control mice treated with KLH (FIG. 5).

Figure 5:
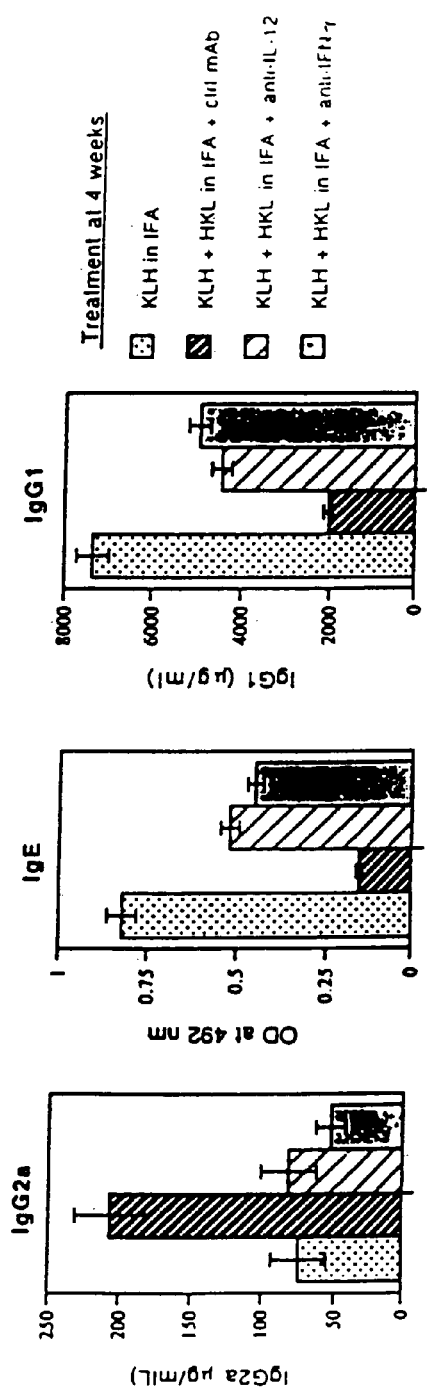
FIG. 5 depicts boosting of KLH/alum-primed mice with HKL as adjuvant increases production of IgG2a anti-KLH antibody and inhibits production of IgE anti-KLH antibody.

Levels of anti-KLH IgG1 antibody in KLH plus HKL treated mice were reduced from those of KLH treated mice (38%, 47% and 72% reduction in three experiments) (FIG. 5). BALB/c mice were primed and immunized as noted in FIGS. 4A and 4B. Seven days after the last injection, mice were bled and their antibody levels determined by ELISA as described above. The values represent the mean±SD of triplicate determinations. For the IgE results, background OD of 0.25 has been subtracted. Representative results from one of four experiments is presented.

The increase in KLH-specific IgG2a by HKL treatment was dependent on the presence of IL-12 and IFN-γ, since neutralization of these cytokines blocked the effects. In contrast, the reduction in IgE synthesis and reduction in KLH-specific IgG1 was only partially dependent on the presence of IL-12 and IFN-γ, since neutralization of IL-12 and IFN-γ only partially restored IgE and IgG1 synthesis. These results demonstrating the effects of HKL on antibody isotype and IgG subclass production demonstrate the HKL as an adjuvant can convert a Th2-dominated immune response into Th1-dominated one, and that the mechanisms by which HKL performs this conversion involves in part IL-12 and IFN-γ.

The data demonstrate that HKL has potent Th1 cytokine-inducing adjuvant activity, and that both primary and established antigen-specific immune responses can be redirected when HKL is included as adjuvant during in vivo vaccination with antigen. In the above experiments, the mixture of HKL with antigen redirected TH2-polarized cytokine synthesis toward Th1 cytokine synthesis, and reduced antigen-specific. IgE production without altering the intensity of the antigen-specific proliferative response. Vaccination with HKL+KLH was remarkably effective in reducing IL4 and IgE synthesis, as the redirected Th1-dominated immune response was observed two weeks after vaccination with HKL+KLH, even after the mice were boosted again with KLH alone to expand IL-4 and IgE producing cells. The present invention exploits the capacity of *Listeria* to induce IL-12 in APC as a means to alter the cytokine profile of ongoing immune responses and limit a TH2-dominated immune response.

HKL as an adjuvant appears to be much more effective in reversing cytokine synthesis in primed CD4+ T cells and in reducing ongoing IgE synthesis than free rIL-12 administered as adjuvant. Although rIL-12 can reduce in vitro IgE synthesis and reduce in vitro IL-4 synthesis, administration of rIL-12 in vivo results in more limited effects, particularly during ongoing Th2 dominated immune responses. In such secondary responses, IL-4 synthesis is often resistant to the effects of rIL-12, and in fact, rIL-12 may increase IL-4 synthesis, perhaps by inducing a rebound increase in IL-10 synthesis. In parasite models, treatment with rIL-12 can resolve ongoing *Leishmania* infection in susceptible BALB/c mice, but only when used in combination with the anti-parasite drug antimony, or only if rIL-12 treatment is started within 14 days of challenge. In contrast, HKL as an adjuvant in our in vivo model system was effective in reducing ongoing IgE and IL-4 synthesis. This effect was due to the induction of endogenous IL-12 production, and independent of IFN-γ.

There are several possible reasons why HKL is much more effective than rIL-12 in reducing ongoing Th2-dominated immune responses. HKL, in contrast to IL-12, reduces IL-10 synthesis (FIG. 3), which may result in enhanced IL-12 production. Furthermore, the adjuvant effects of HKL may be localized to sites of antigenic stimulation, whereas the effects of rIL-12, which diffuses rapidly into the systemic circulation, is more widespread in the host, less antigen-specific, and appears to evoke sustained NK cell activation. Another reason for the effectiveness of HKL as an adjuvant is that HKL may induce the production of several cytokines in addition to IL-12, such as IL-18, which is 10 fold more potent than IL-12 in inducing IFN-γ, and which is also extremely effective in reducing IgE synthesis in B cells.

The effectiveness of HKL as an adjuvant in reducing Th2-dominated immune responses and reducing antigen-specific IgE synthesis suggests that it is clinically useful in the treatment of diseases caused by heightened allergen-specific Th2 responses, such as allergy and asthma. Allergen immunotherapy, currently performed by vaccination with aqueous extracts of allergen, is used as an effective therapy for these two diseases, although treatment failures are frequent. Since disease improvement with allergen immunotherapy is associated with the reduction of allergen-specific IL-4 synthesis, and since HKL is potent in reducing antigen-specific Th2 dominated immune responses and antigen-specific IgE synthesis, modification of conventional allergen immunotherapy to include adjuvants such as HKL may render allergen immunotherapy much more efficacious.

Data also indicate that immunotherapy with HKL as adjuvant can reduce allergen-induced airway hyperreactivity in an allergen-induced murine model. Mice treated with ovalbumin and *Listeria* in IFA display significantly reduced airway hyperreactivity as compared to mice receiving ovalbumin in IFA without *Listeria*. Safety issues with *Listeria* are not of major concern, since killed rather than live *Listeria* is effective, and also since even live *Listeria* is not a particularly invasive organism. Therefore, *Listeria* adjuvants are effective for allergen immunotherapy, and elicit rapid innate immune system activation and production of Th1-inducing and Th2-reducing cytokines on vaccination.

Example 2

Vaccination with Heat Killed *Listeria* as Adjuvant Reverses Established Allergen-Induced Airway Hyperreactivity and Inflammation In murine model of asthma, HKL as an adjuvant given once with antigen prevented the development of airway hyperreactivity and airway inflammation in OVA-immunized BALB/c mice and significantly reduced airway eosinophilia and mucus production. Moreover, when given late after allergen-sensitization, and single dose of HKL with antigen reversed established airway hyperreactivity and reduced air inflammation. The inhibitory effect on airway hyperreactivity depended on the presence of IL-12 and on CD8+ T cells, was associated with an increase of the IL-18 mRNA expression, and required close association between HKL and the antigen. Thus, these results demonstrate that HKL as an adjuvant very effectively promotes protective immune responses in the respiratory tract, and down-modulates ongoing Th2-dominated responses, indicating that HKL as an adjuvant for allergen immunotherapy can be clinically effective in the treatment of allergic asthma.

Materials and Methods

Animals: BALB/cByJ mice were obtained from the Jackson Laboratory, Bar Harbor, Me. The Stanford University Committee on Animal Welfare approved animal protocols used in this study.

Monoclonal Antibodies: Monoclonal antibodies were purified from ascites by ammonium sulfate precipitation and ion-exchange chromatography. The following hybridomas were used: R46A2 (anti-IFN-γ mAb), and 53.6.7 (anti-CD8+) obtained from ATCC (American Type Culture Collection, Rockville, Md.); XMG1.2 (anti-IFN-γ antibody), TRFK-4 and TRFK-5 (anti-IL5 mAbs); BVD4-1 D11, BVD6-24G2 (anti-IL-4 mAb); C17.8 (anti-IL12 mAb). Anti-38C13 idiotype mAb 4G10 (rat IgG2a) was used as isotype control.

Immunizations

Protocol 1 (prevention of airway hyperreactivity): BALB/c mice were primed in the footpads with OVA (50 μg/mouse) adsorbed to 2 mg of alum (Al[OH]$_3$). Four weeks later (day 29) mice were injected in the footpads with 200 μg OVA in IFA, or with 200 μg OVA plus $10^8$. HKL in IFA. Mice also received 50 μg OVA in 50 μl NaCl 0.9% intranasally on day 29. After an additional 10 days (day 39) all mice received a 100 μg booster immunization of OVA in PBS in the footpads, and were challenged with OVA (50 μg) in PBS intranasally on the same day and the two following days (day 40, 41). One day after the last intranasal challenge with OVA, airway hyperreactivity was measured from conscious mice after inhalation of increasing concentrations of methacholine in a whole body plethysmograph (day 42). After an additional four days, mice were sacrificed with a lethal dose of phenobarbital (450 mg/kg), blood was taken, bronchoalveolar lavage (BAL) was performed, lungs were removed and fixed and lymphocytes were isolated from the draining lymph nodes (LN) for in vitro culture (day 46).

Protocol 2 (reversal of established airway hyperreactivity): In experiments designed to determine whether HKL as an adjuvant could reverse established airway hyperreactivity rather than inhibit the development of airway hyperreactivity, mice received HKL ($10^8$ per mouse) mixed with OVA in IFA with the second boost instead of the first boost (day 39 instead of day 29). Airway hyperreactivity was measured one day before, three days, and ten days after the injection of HKL. On day 50 mice received a final subcutaneous boost with OVA (50 μg in PBS) and were sacrificed four days later for BAL and lung fixation.

To facilitate pulmonary aspiration during intranasal administration of antigen, mice were lightly anesthetized intraperitoneally (i.p.) with 0.25 ml of ketamine (0.44 mg/ml)/xylazine (6.3 mg/ml) in normal saline. 75% of the intranasally administered antigen can be subsequently detected in the lungs (Tsuyuki et al., (1997) *J. Exp. Med.* 185:1671–9.

Treatment of mice with anti-cytokine antibodies: BALB/c mice were injected i.p. with 1 mg of mAb C17.8 (for IL-12 depletion), mAb 53.6.7 (for CD8+ depletion) or 4G10 (rat IgG2a control) in 0.5 ml PBS one day before, the day of, and 3 days following immunization with OVA in IFA or OVA in IFA with HKL, according to the immunization schedule of Protocol 1.

Restimulation of lymph node cells in vitro. Draining lymph nodes were removed and depleted of resting B cells by adherence to goat anti-mouse Ig-coated plates. $5 \times 10^5$ lymph node cells were restimulated in vitro with OVA in DMEM (Life Technologies, Grand Island, N.Y.), which was supplemented as previously described (Clayberger et al. (1983) *J. Exp. Med.* 157:1906), and contained $5 \times 10^{-5}$ M 2-mercaptoethanol and 10% FCS (HyClone Laboratories, Logan, Utah). Cells were cultured in 96 well microtiter plates in 150 μl medium. Supernatants were harvested after four days for determination of IL-4, IL-10, and IFN-γ levels. Cytokine content in each sample was measured in triplicate by ELISA.

Cytokine ELISA. ELISAS were performed as previously described Macaulay et al. (1998) *J. Immunol.*

160:1694–1700. The antibody pairs used were as follows, listed by capture/biotinylated detection: IL-4, BVD4-1D11/BVD6-24G2; IFN-γ, R4-6A2/XMG1.2. Recombinant cytokine were used as standards, with curves generated in 1:2 dilutions from 500 to 39 pg/ml for IL-4, and 20-2, 156 ng/ml for IFN-γ.

Measurement of anti-OVA antibody isotypes. Mice were bled at the time of sacrifice and OVA-specific antibody was measured using a modified antigen-specific ELISA. For measurement of OVA specific IgG, plates were coated overnight with 5 μg/ml OVA. After washing and blocking, serial diluted sera were added to the plates. Following overnight incubation, the plates were developed using HRPO-conjugated goat anti-IgG subclass-specific antibodies (Southern Biotechnology Associates, Birmingham, Ala.). After additional washing, OPD substrate was added, the plates developed and the OD determined at 492 nm. Anti-OVA IgG1 mAb 6C1 and anti-OVA IgG2a mAb 3A11 were used as standards for quantitation of each IgG subclass. Determination of OVA-specific IgE was performed by ELISA, using rat anti-mouse IgE mAb EM95 (5.0 μg/ml) to coat plates. After the samples were applied and incubated overnight, plates were washed and biotinylated OVA (10 μg/ml) was added. Two hours later, plates were washed and HRPO-conjugated streptavidin (Southern Biotechnology Associates) was added. Plates were developed with OPD substrate and the OD determined at 492 nm. Sera from mice hyperimmunized with OVA in alum was quantitated for IgE and used as standard for the OVA-specific IgE ELISA.

Preparation of heat-killed *Listeria monocytogenes* (HKL). HKL were prepared as described in Example 1. A clinical isolate of *Listeria monocytogene* was grown in nutrient broth cultures (Difco, Detroit, Mich.) overnight at 37° C. on a rotator. Cultures in log phase growth were harvested, centrifuged, and washed three times in PBS. The recovered bacteria were resuspended in PBS and incubated at 80° C. for one hour. After two additional washes in PBS, absence of viable colonies was confirmed by lack of growth on nutrient agar plates. Bacteria concentration was enumerated by comparing the absorbance of a serial dilution of HKL at 570 nm compared with a standard dilution of a known concentration of *Listeria* previously enumerated by counting the outgrowth of colonies from serial dilutions of bacteria plated on nutrient agar.

Preparation of splenic adherent cells. Spleen cells were cultured at 5×10⁶/ml in cDME medium in 24 well tissue culture plates for 2–3 hrs at 37° C. The nonadherent cells were removed by washing with warm cDME until visual inspection revealed a lack of lymphocytes (>98% of the cell population).

RNA isolation and IL-18 RT-PCR Assay Splenic adherent cells cultured with HKL (10⁸/ml) for 8, 16, or 24 hrs, and popliteal lymph node cells taken from mice 12 and 24 hours after footpad injection of 10⁸ HKL were analyzed for IL-18 mRNA expression. Cells were processed using Qiagen RNA isolation kits (Qiagen, Valencia, Calif.). Reverse transcription was performed with 200 ng of RNA, 2 μg of oligo (dT) (Life Technologies) and 1 unit of Superscript II Reverse transcriptase at 60° C. for 60 minutes. Samples were stored at −20° C. until further use.

Primers specific for β-actin and IL-18 (Bohn et al. (1998) *J. Immunol.* 160:299–307) were synthesized. cDNA (10 ng) was mixed with 10× buffer, dNTPs (0.2 mM final), MgCl₂ (2.5 mM final), 5' and 3' primers, and Taq DNA polymerase (1 unit/reaction, Life Technologies) in a final volume of 25 μl. PCR was performed in a DNA thermal cycler (MJ Research) for 30 cycles, and products were visualized by electrophoresis. Data shown are representative of three experiments.

Measurement of Airway Responsiveness. Airway responsiveness was assessed by methacholine-induced airflow obstruction from conscious mice placed in a whole body plethysmograph (model PLY 3211, Buxco Electronics Inc., Troy, N.Y.). Pulmonary airflow obstruction was measured by Penh using the following formula:

$$Penh = \left(\frac{Te}{RT} - 1\right) \times \left(\frac{PEF}{PIF}\right),$$

where Penh=enhanced pause (dimensionless), Te=expiratory time, RT=relaxation time, PEF=peak expiratory flow (ml/s), and PIF=peak inspiratory flow (ml/s) (Hamelmann et al. (1997) *Am. J. Respir. Crit. Care Med.* 156:766–75. Enhanced pause (Penh), minute volume, tidal volume, and breathing frequency were obtained from chamber pressure, measured with a transducer (model TRD5100) connected to preamplifier modules (model MAX2270) and analyzed by system XA software (model SFT 1810). Measurements of methacholine responsiveness were obtained by exposing mice for 2 min to NaCl 0.9%

Collection of BAL Fluid and Lung Histology. Animals were injected i.p. with a lethal dose of phenobarbital (450 mg/kg). The trachea was cannulated, and the lung was then lavaged with 0.8 ml of PBS three times, and the fluid pooled. Cells in the lavage fluid were counted using a hemocytometer and BAL cell differentials were determined on slide preparations stained with Hansel Stain (Lide Laboratories, Florissant, Mo.). At least 200 cells were differentiated by light microscopy based on conventional morphologic criteria. In some animals, no BAL was performed but lungs were removed, washed with PBS, fixed in 10% formalin and stained with hematoxylin and eosin.

Results

HKL as an adjuvant inhibits the development of airway hyperreactivity in OVA-immunized BALB/c mice. It was previously demonstrated that immunization of mice with *Listeria monocytogenes* as adjuvant successfully biased the development of antigen-specific cytokine synthesis toward Th1 cytokine production in both primary and secondary immune responses. Since the pathogenesis of asthma is tightly associated with Th2 cytokines, and since Th1 cytokines may protect against asthma, the ability of heat killed *Listeria monocytogenes* (HKL) to inhibit the development of airway hyperreactivity in OVA-immunized BALB/c mice was investigated.

Figure 6:
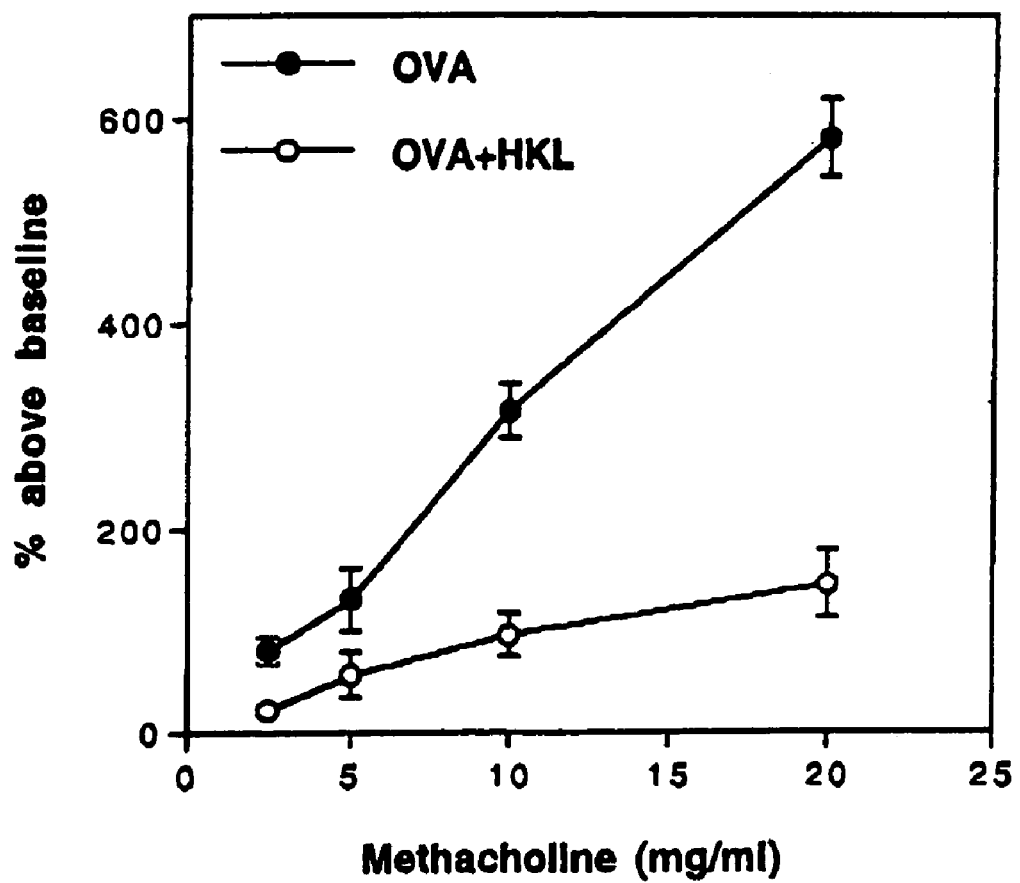
FIG. 6 shows that HKL as an adjuvant inhibits the development of airway hyperreactivity in OVA-immunized BALB/c mice.

BALB/c mice were immunized subcutaneously with OVA adsorbed to alum, which provokes an ovalbumin-specific Th2-dominated immune response. The mice were then boosted with OVA with or without HKL. Furthermore, to induce airway hyperreactivity, mice were also challenged with OVA intranasally, following which airway hyperreactivity was measured in a whole body plethysmograph by challenge with increasing concentrations of methacholine. FIG. 6 demonstrates that immunization of BALB/c mice with OVA subcutaneously and intranasally resulted in the development of significant airway hyperreactivity. BALB/c mice were primed according to Protocol 1, FIG. 1. One day after the last intranasal challenge with OVA, airway hyperreactivity in response to increasing concentrations of methacholine was measured from conscious mice placed in a whole body plethysmograph. Data are expressed as percent above baseline (mean±SEM); n≧10 for each data point. OVA-primed mice immunized with OVA plus HKL as an adjuvant at the time of the first boost showed dramatically reduced airway hyperreactivity, indicating that HKL as an adjuvant inhibited the development of airway hyperreactivity in OVA-immunized BALB/c mice.

BALB/c mice were immunized with OVA in IFA±HKL according to protocol 1. Lung tissue was fixed in formalin and stained with hematoxylin and eosin (H&E) at the day of sacrifice (day 46). Upper Panel FIG. 7: Lung tissue from BALB/c mice after immunization with OVA revealed dense peribronchiolar mononuclear cell infiltrates consisting of lymphocytes, eosinophils and some neutrophils. The bronchus lumen is filled with mucus. H&E, x250. Lower Panel: Lung tissue from BALB/c mice after immunization with OVA+HKL had only minimal lung disease with very few lymphocytes and almost no mucus production. H&E, x250.

Figure 7:
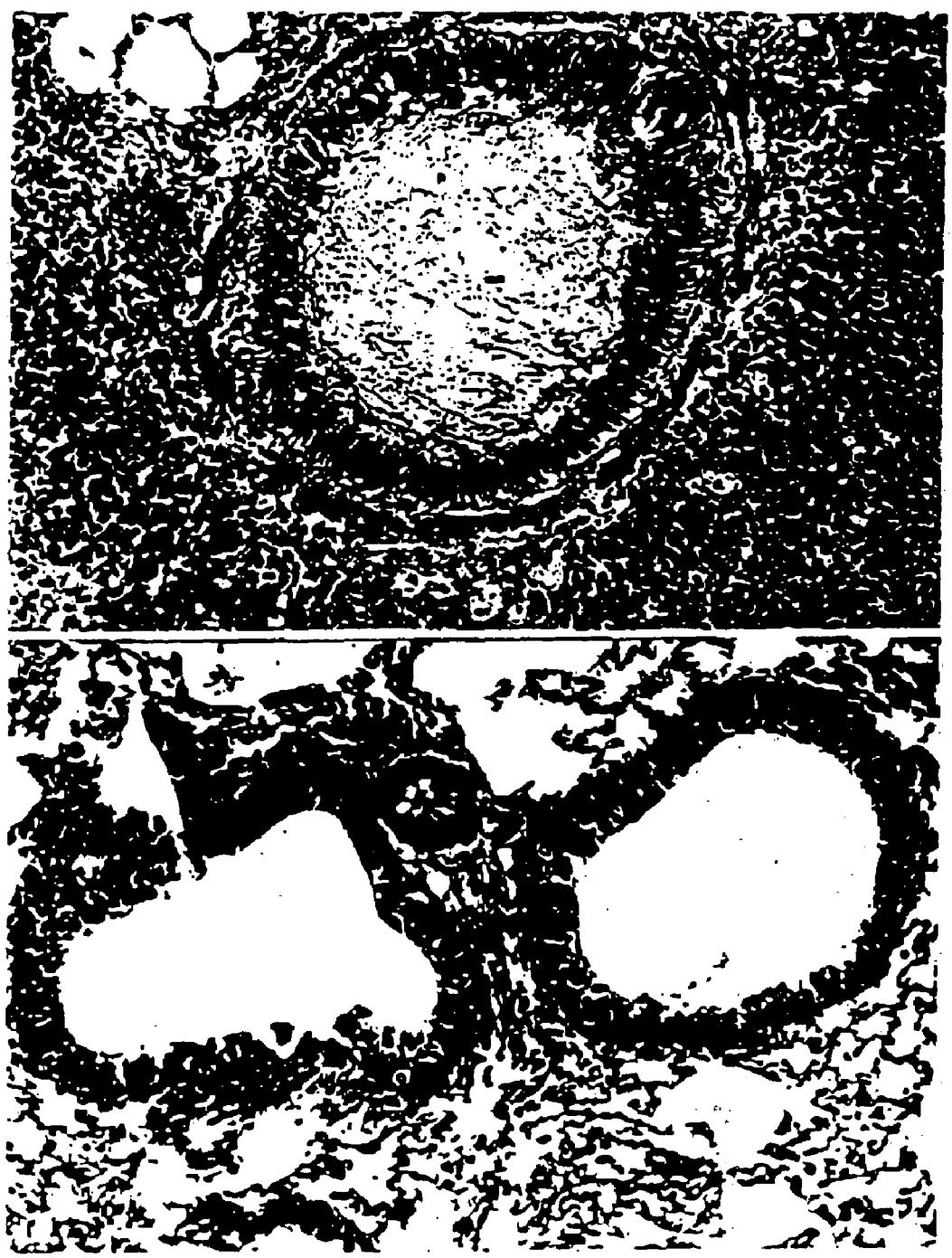
FIG. 7 illustrates that HKL is an adjuvant significantly reduces airway inflammation in OVA-immunized BALB/c mice.

HKL as an adjuvant significantly reduces airway inflammation in OVA-immunized BALB/c mice. At the day of sacrifice, lung histology was examined after fixation and staining with hematoxylin and eosin. Lung sections from BALB/c mice that were immunized with OVA without HKL as an adjuvant showed significant airway inflammation with peribronchiolar and perivascular infiltrates, consisting of lymphocytes, eosinophils and some neutrophils (FIG. 7, upper panel). In contrast, lung sections from mice that were immunized with OVA and HKL as adjuvant showed almost normal lung histology, with only marginal perivascular and peribronchiolar lymphocytic infiltrates (FIG. 7, lower panel). Thus, HKL as adjuvant during the immunization significantly reduced airway inflammation in OVA-immunized BALB/c mice.

Figure 8:
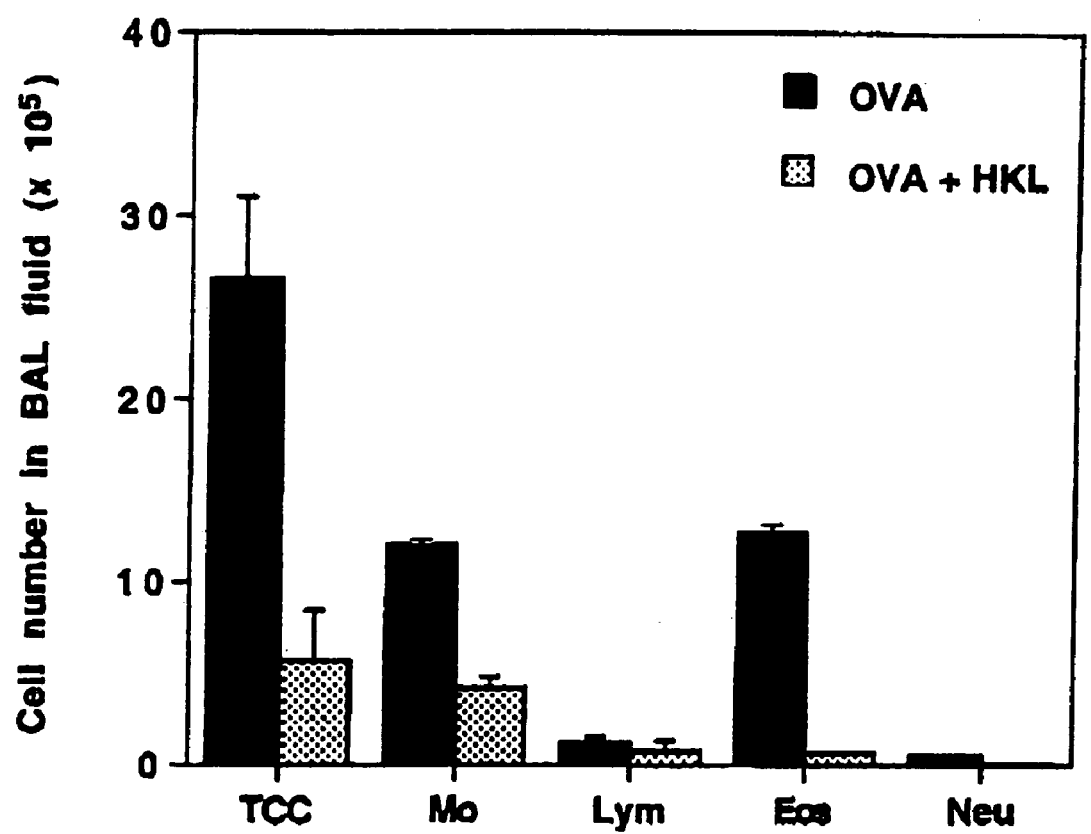
FIG. 8 shows that HKL as an adjuvant significantly reduces the total cell number and the relative number of eosinophils in BAL fluid of OVA-immunized BALB/c mice.

HKL as an adjuvant significantly reduces the total cell number and eosinophilia in BAL fluid of OVA-immunized BALB/c mice. The histopathologic analysis was extended by examination of the cell numbers and types in the BAL fluid, which was harvested five days after the last intranasal challenge with OVA. The total number of cells recovered in the BAL fluid of BALB/c mice boosted with OVA plus HKL as an adjuvant was significantly lower than that in the control group (FIG. 8). Furthermore, vaccination with HKL as an adjuvant in the immunization protocol significantly reduced the proportion of eosinophils from 48% in the control group to 11% in HKL treated mice (FIG. 8). These results demonstrate that HKL as an adjuvant significantly reduces the total cell number and the proportion of eosinophils recovered in the BAL fluid of OVA-immunized mice and confirm the results observed with lung histology.

BALB/c mice were immunized with OVA subcutaneously and intranasally according to Protocol 1. BAL was performed one day after measurement of airway hyperreactivity (day 43) with three aliquots of 0.8 ml PBS per mouse. The relative number of different types of leukocytes (lung cell differentials) was determined from Hansel Stain slide preparations of BAL fluid. The data are expressed as mean±SEM of each cell type in BAL fluid derived from differentials based on 200 cells (n≧6 for each group).

Figure 9:
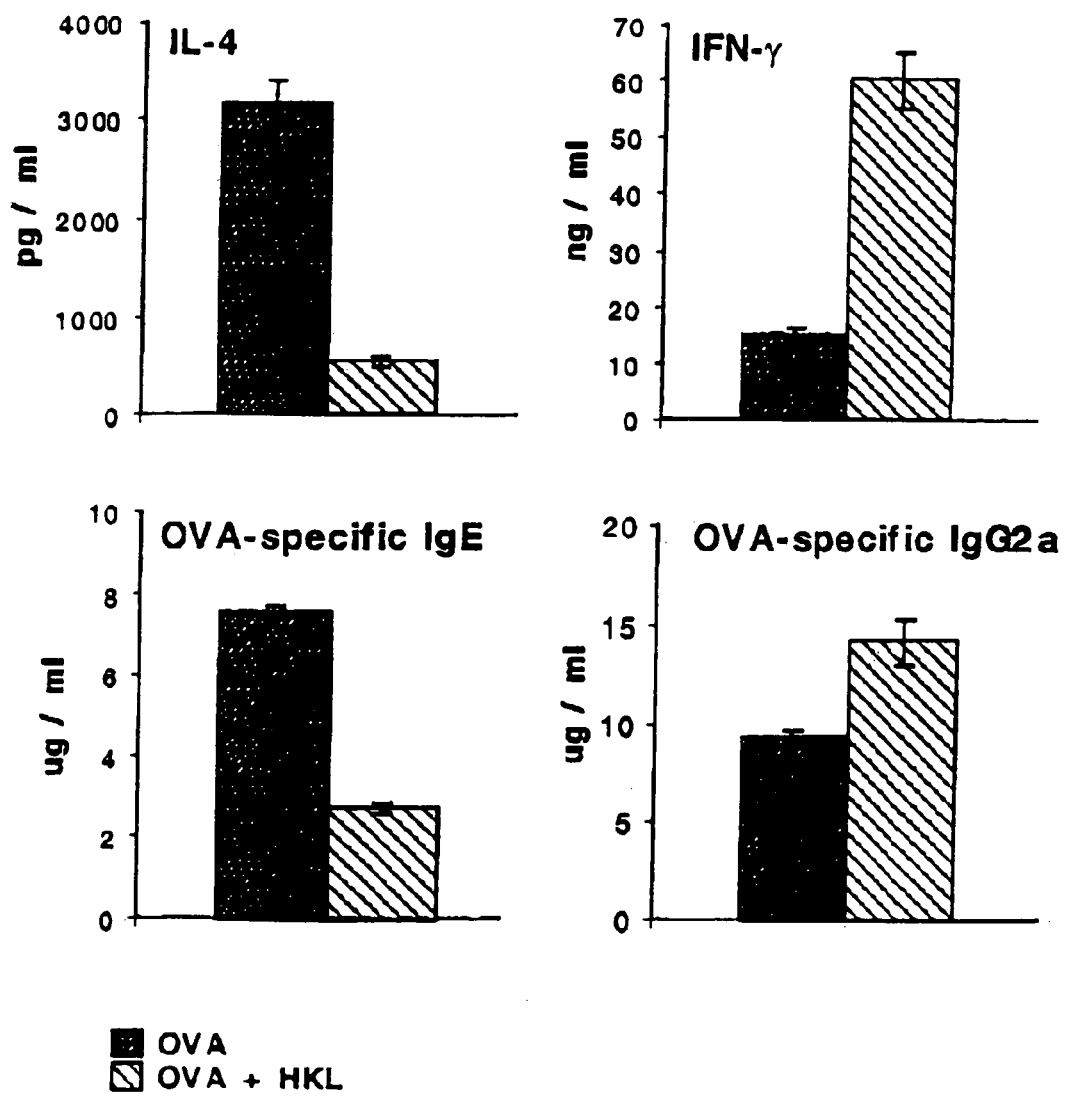
FIG. 9 shows that HKL as an adjuvant converts an established Th2-to a Th1 like cytokine response and inhibits the production of OVA-specific IgE.

HKL as an adjuvant elicits a Th1 like cytokine response. To determine if the reduced airway hyperreactivity in mice immunized with HKL as adjuvant correlated with alteration of cytokine profiles in CD4+ T cells, mice were sacrificed four days after measurement of airway hyperreactivity. Draining lymph nodes were removed and lymph node cells were stimulated with OVA in vitro. FIG. 9 shows that cells from mice immunized with OVA subcutaneously and intranasally produced high levels of IL-4 and low levels of IFN-γ.

In contrast, immunization with OVA plus HKL as adjuvant inhibited IL-4 production and greatly enhanced IFN-γ synthesis.

FIG. 9: BALB/c mice were immunized with OVA subcutaneously and intranasally according to Protocol 1. Mice were bled seven days after the last subcutaneous injection, and lymph node cells were removed and cultured at $5 \times 10^5$ cells/well with 100 μg/ml OVA. IL-4, IL-10 and IFN-γ levels in supernatants were determined after four days by ELISA. Serum antibody levels were determined by ELISA. Data are the mean of triplicate cytokine determinations±standard deviation. Representative results from one of three experiments are presented.

The isotype and subclass distribution of anti-OVA antibody responses in serum collected on day 46 was also analyzed. FIG. 9 shows that vaccination with OVA plus HKL adjuvant greatly reduced anti-OVA IgE antibody responses and enhanced anti-OVA IgG2a antibody responses as compared to control mice immunized with OVA alone. Levels of anti-OVA IgG1 antibody were not significantly different in the two groups.

Figure 10:
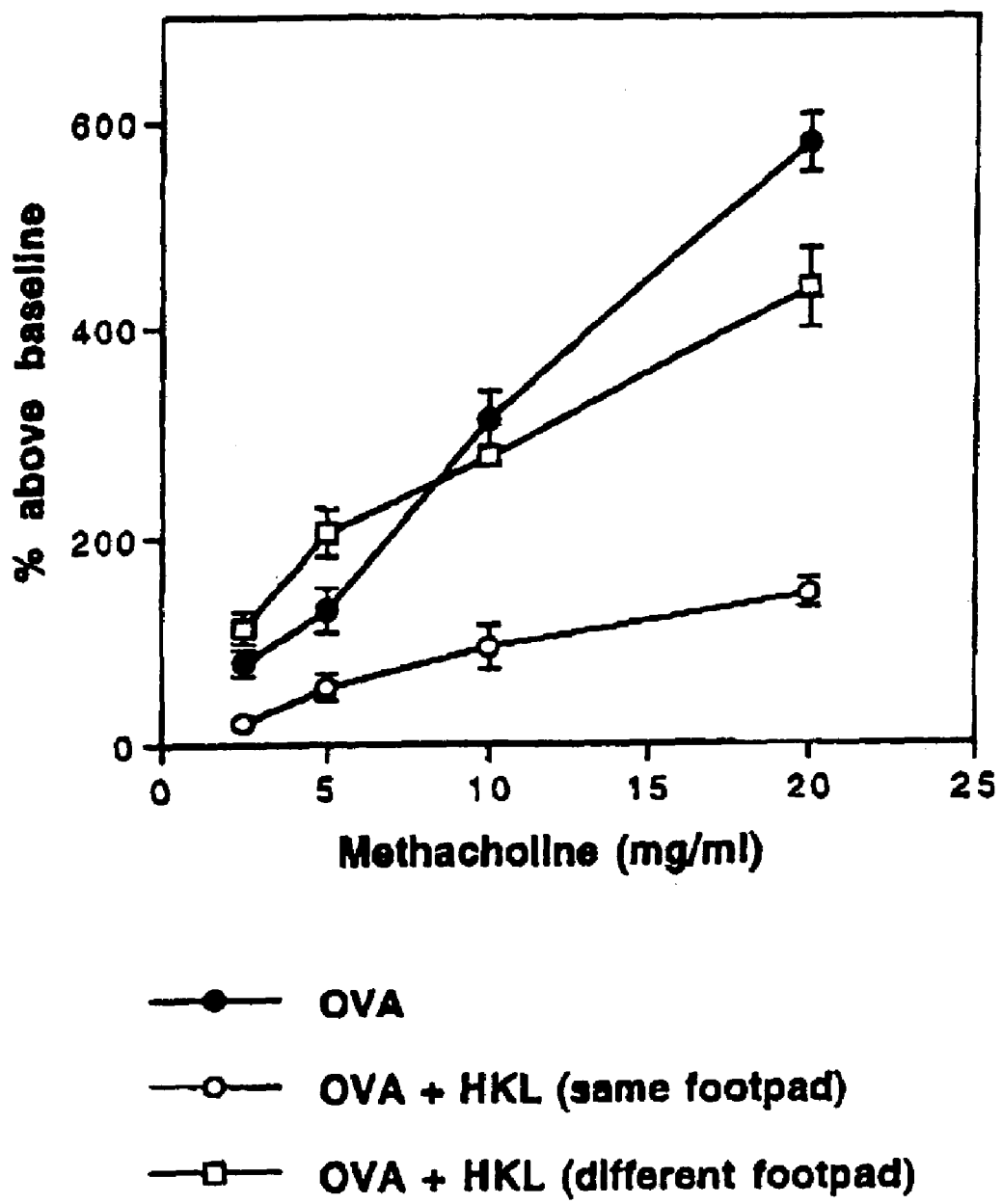
FIG. 10 shows that HKL is most efficient as adjuvant when mixed with the antigen before administration.

HKL should be in close physical association with OVA to inhibit responses. To determine whether HKL had a generalized effect on immune responses or affected only responses to antigens in close physical association with it, mice were immunized with HKL and OVA in separate footpads. FIG. 10 shows that mice which received HKL and OVA together in the same footpad showed greatly reduced airway hyperreactivity, while mice which received the HKL in a different footpad from the OVA showed only minimal reduction in airway hyperreactivity. When HKL and OVA were injected separately in different footpads, the reduction of IL-4 and the increase of IFN-γ were about 50% of that when administered together. Thus, the inhibition of airway hyperreactivity in OVA-primed mice was most efficient when HKL and the antigen were in close physical association with each other.

FIG. 10: Mice were immunized essentially as described in Protocol 1. Four weeks after the initial footpad priming with 50 μg OVA adsorbed to 2 mg alum, one group of mice received OVA in IFA and HKL in IFA in opposite footpads. Other groups of mice received OVA in IFA or OVA mixed with HKL in IFA in both footpads. All mice received a total of 50 μg OVA. One day after the last intranasal challenge with OVA, airway hyperreactivity in response to increasing concentrations of methacholine was measured from conscious mice placed in a whole body plethysmograph. Data are expressed as percent above baseline (mean±SEM); n≧6 for each data point.

Figure 11A:
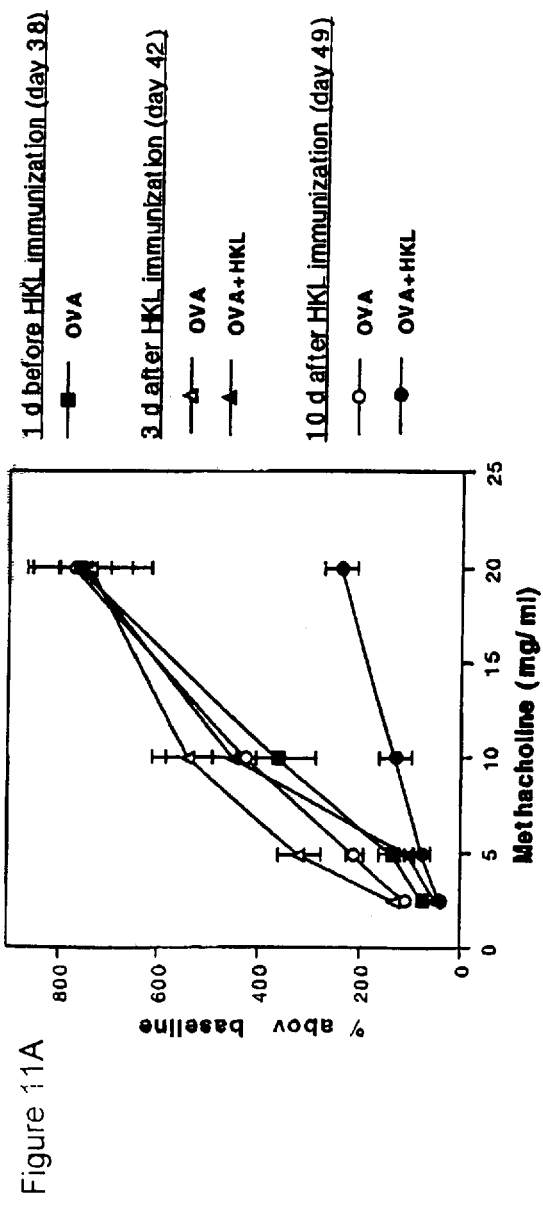
FIGS. 11A and 11B show that HKL as an adjuvant reverses established airway hyperreactivity in OVA-immunized BALB/c mice.

HKL as an adjuvant reverses established airway hyperreactivity in OVA-immunized BALB/c mice. To determine whether HKL as an adjuvant could reverse established airway hyperreactivity in addition to inhibiting the development of airway hyperreactivity, mice were boosted with OVA plus HKL on day 39, after the establishment of airway hyperreactivity (Protocol 2). FIG. 11A shows that airway hyperreactivity was present prior to administration of HKL, but 10 days after administration of HKL with OVA there was a significant reduction in airway hyperreactivity. This protective effect with HKL could not be detected 3 days after the mice had received HKL, indicating that it required at least 10 days after administration of HKL to develop. Control mice which received OVA without HKL showed high airway hyperreactivity at all time points.

FIG. 11A: To determine whether HKL as an adjuvant could reverse established airway hyperreactivity, BALB/c mice were immunized by Protocol 2. Mice received OVA in IFA or OVA mixed with HKL ($10^8$ per mouse) in IFA with the second boost instead of the first boost (day 39 instead of day 29). Airway hyperreactivity in response to increasing concentrations of methacholine was measured one day before, three days, and ten days after the injection of HKL from conscious mice placed in a whole body plethysmograph. Data are expressed as percent above baseline (mean±SEM); $n \geq 6$ for each data point.

Figure 11B:
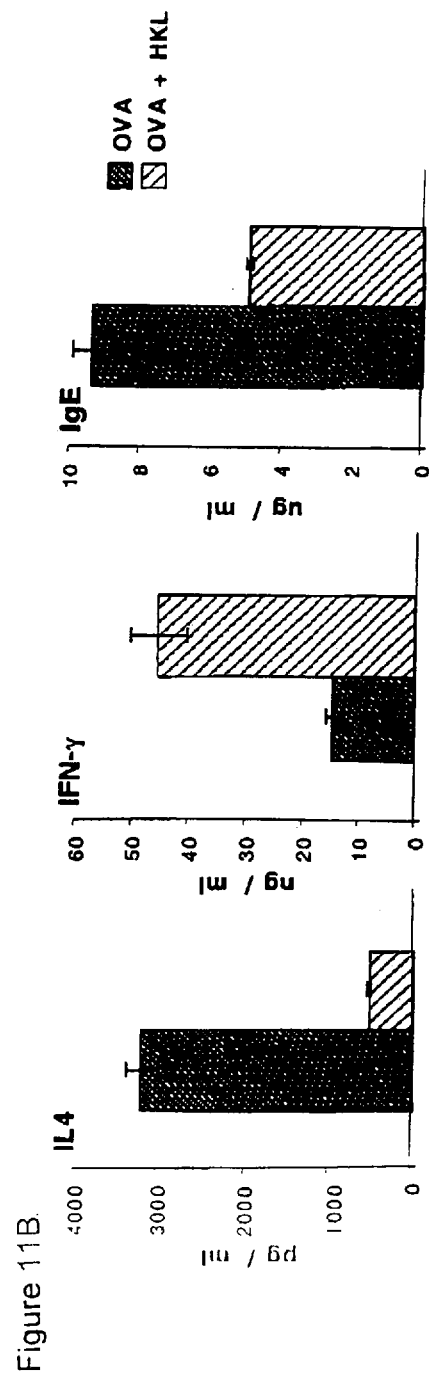

FIG. 11B: On day 50 mice received a final subcutaneous boost with OVA (50 µg in PBS). Mice were bled four days later, and lymph node cells were removed and cultured at $5 \times 10^5$ cells/well with 100 µg/ml OVA. IL-4, IL-10 and IFN-γ levels in supernatants were determined after four days by ELISA. Serum antibody levels were determined by ELISA. Data are the mean of triplicate cytokine determinations standard deviation. Representative results from one of three experiments are presented.

Analysis of the cytokine profiles of lymph node cells obtained on day 54 and stimulated with OVA in vitro showed that HKL increased OVA-specific IFN-γ production, and decreased OVA-specific IL4 and IgE production (FIG. 11B). These results demonstrate that HKL as an adjuvant not only prevents the development of airway hyperreactivity when given during the earlier phase of the immunization protocol but also reverses established airway hyperreactivity and the cytokine profiles of CD4+ T cells.

The effect of HKL on the development of airway hyperreactivity is mediated by CD8+ T cells. To investigate the mechanism by which HKL affected OVA-specific responses, blocking antibody to IL-12 or depleting antibody to CD8+ T cells were administered during the immunization protocol. As expected, mice immunized with OVA had high airway reactivity, which was reduced by vaccination with OVA+ HKL in the presence of a control mAb (FIG. 12A).

Figure 12A:
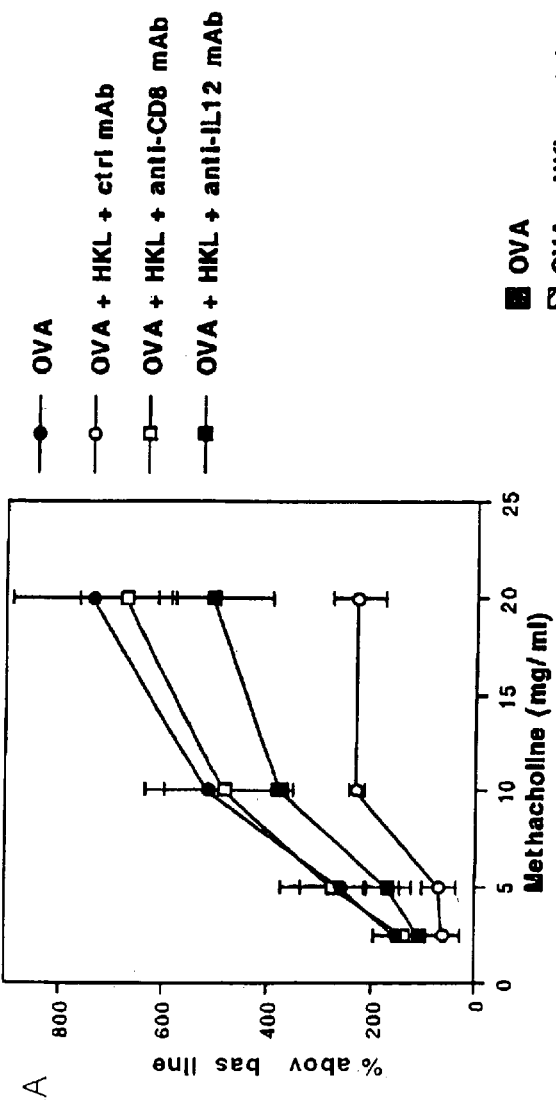
FIGS. 12A and 12B show that inhibition of the development of airway hyperreactivity by HKL as adjuvant depends on IL-12 and $CD8^+$ cells.

FIG. 12A: BALB/c mice were immunized according to the immunization schedule of Protocol 1. Mice were injected i.p. with 1 mg of mAb C17.8 (for IL-12 depletion), mAb 53.6.7 (for CD8+ depletion) or 4G10 (rat IgG2a control) in 0.5 ml PBS one day before, the day of, and 3 days following immunization with OVA in IFA or OVA mixed with HKL ($10^8$ per mouse) in IFA. One day after the last intranasal challenge with OVA, airway hyperreactivity in response to increasing concentrations of methacholine was measured from conscious mice placed in a whole body plethysmograph. Data are expressed as percent above baseline (mean±SEM); $n \geq 6$ for each data point.

Figure 12B:
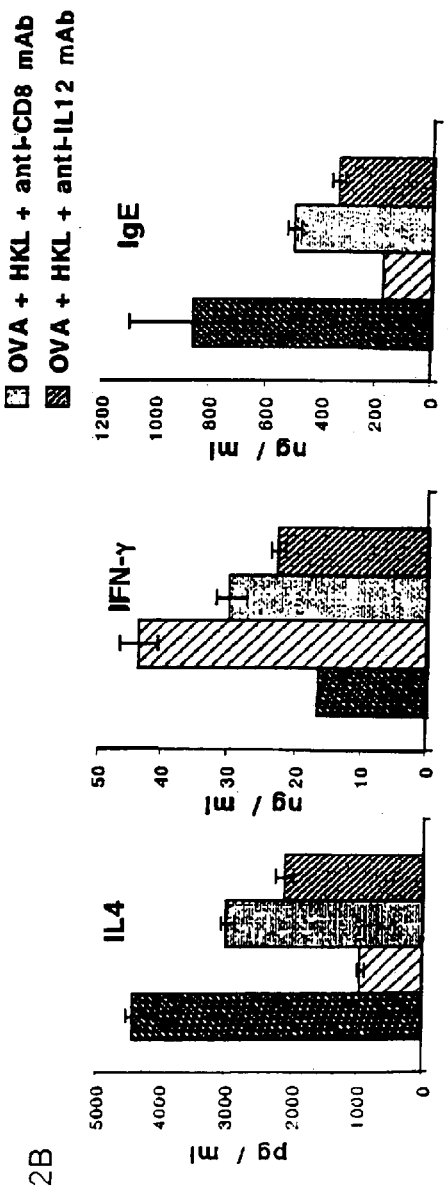

FIG. 12B: Mice were bled seven days after the last subcutaneous injection, and lymph node cells were removed and cultured at $5 \times 10^5$ cells/well with 100 µg/ml OVA. IL-4, IL-10 and IFN-γ levels in supernatants were determined after four days by ELISA. Serum antibody levels were determined by ELISA. Data are the mean of triplicate cytokine determinations±standard deviation. Representative results from one of three experiments are presented.

Treatment with anti-CD8 mAb reversed the effect of HKL as adjuvant and restored OVA-induced airway hyperreactivity. Treatment with anti-IL-12 mAb partly eliminated the effect of HKL on airway hyperreactivity in OVA-immunized mice. In addition, the reduction by HKL of OVA-specific IgE levels was partially reversed by treatment with either anti-CD8 or anti-IL12 mAb (FIG. 12B). Furthermore, treatment of mice with anti-CD8 mAb partially reversed the effect of HKL on IFN-γ and IL-4 production. These results indicate that both CD8+ T cells and IL-12 play a role in the immunomodulatory effects of HKL on the airway hyperreactivity.

Figure 13A:
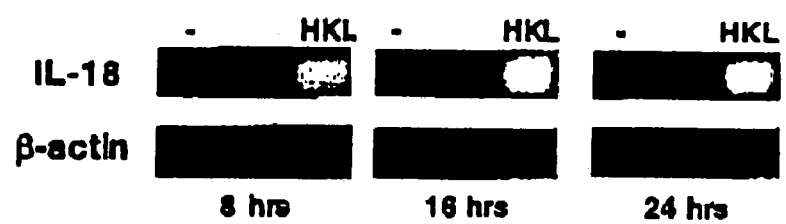
FIGS. 13A and 13B shows that HKL as an adjuvant increases IL-18-mRNA expression in spleen cells in vitro as well as in vivo.
Figure 13B:
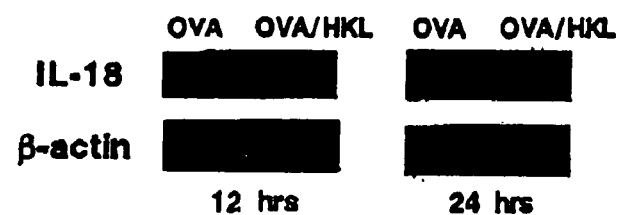

HKL as an adjuvant increases IL-18-mRNA expression in spleen cells in vitro and in vivo. Since HKL, as adjuvant strongly induced IFN-γ production (FIGS. 13A and 13B), it was determined whether HKL also increased IL-18 production. IL-18 mRNA levels were analyzed by semiquantitative PCR analysis in splenic adherent cells cultured in vitro with HKL. Semiquantitative assessment of β-actin and IL-18 mRNA production by RT-PCR (30 cycles). FIG. 13A: Splenic adherent cells were cultured with HKL ($10^8$/ml) for 6, 18 or 24 hrs. and analyzed for IL-18 mRNA expression. FIG. 13B: Popliteal lymph node cells were isolated from BALB/c mice 12 and 24 hours after footpad injection of $10^8$ HKL and were analyzed for IL-18 mRNA expression.

FIG. 13A demonstrates that HKL induced a significant quantity of IL-18 mRNA expression after 8, 16 and 24 hours of culture. Moreover, treatment of mice in vivo with OVA and HKL, but not with OVA alone, induced IL-18 mRNA expression in draining lymph nodes (FIG. 13B). The mRNA expression was detected 24 hours but not at 12 hrs after immunization. These data indicate that the induction of IL-18 expression is associated with the immunomodulatory effects of HKL.

DISCUSSION

The above results demonstrate that heat-killed *Listeria monocytogenes*(HKL) as adjuvant very effectively inhibits airway hyperreactivity and airway inflammation. These effects were accompanied by the conversion of an antigen-specific Th2-dominated immune response into an antigen-specific Th1-like immune response, and by a dramatic decrease of antigen-specific IgE. Moreover, HKL as adjuvant not only prevented, but also reversed ongoing, airway hyperractivity and inflammation. These observations demonstrate that HKL can be an adjuvant for the improvement of allergen immunotherapy, and suggest that patients with allergic asthma will benefit from such a therapeutic agent.

Asthma is characterized by the over production of the Th2 cytokines IL-4, IL-5 and IL-13, which initiate and sustain the allergic asthmatic inflammatory response by enhancing the production of IgE and the growth, differentiation, and recruitment of mast cells, basophils, and eosinophils. The Th2 driven inflammatory process may be a consequence of a relative insufficiency in IFN-γ production, since IFN-γ can inhibit the development of Th2 responses. In addition, clinical studies demonstrated that reduced IFN-γ secretion in neonates is associated with the subsequent development of atopy. Furthermore, a predisposition towards the overproduction of Th1 cytokines may protect against atopy, since patients with multiple sclerosis, rheumatoid arthritis or infection with tuberculosis (conditions associated with increased production of Th1 cytokines) have a reduced predisposition toward the development of atopy.

Immunotherapies and immune modulatory approaches that enhance Th1-dominated responses appear to be beneficial for allergic individuals, and in animal models of allergic disease. Immunotherapies in these models, however, while effective in preventing the development of airway hyperreactivity, have not been shown to reverse established airway hyperractivity. In contrast, the present data describes an immunotherapy that is highly effective in reversing ongoing airway hyperractivity. This reversal of airway hyperractivity with HKL as adjuvant was associated with a significant increase in IFN-γ production and a significant reduction of IL-4 and allergen-specific IgE production. The reversal in airway hyperreactivity with HKL as an adjuvant required only one dose of the HKL plus antigen, indicating that immunotherapy with HKL can be effective in patients with asthma, who by definition have ongoing airway hyperractivity.

The potent capacity of HKL to reverse established airway hyperractivity and inflammation may be attributed to the fact that HKL activates multiple immunological mechanisms. *Listeria monocytogenes* is a gram positive, facultative intracellular bacterium, which elicits a strong classical cell-mediated immune response, characterized by the presence of potent antigen-specific CD8+ killer cells. The *L. monocytogenes* proteins listeriolysin 0 and p60 are processed through the MHC class I pathway and stimulate protective CD8+ cytotoxic T lymphocyte (CTL) responses. In the present model system, CD8+ T cells induced by HKL plus antigen may play an important role in down modulating airway hyperreactivity, since treatment with anti-CD8 mAb reversed the inhibitory effect of HKL on airway hyperreactivity.

The *Listeria* cell wall component lipoteichoic acid potently induces IL-12 production in macrophages. IL-12 in turn stimulates the production of IFN-γ by NK cells and T cells, which further enhances Th1 CD4+ T-cell development, activates microbicidal activity of macrophages, and promotes the development of cell-mediated immune responses. Moreover, these data demonstrate that HKL not only induces the production of IL-12 but also stimulates the secretion of IL-18. IL-18 is a product of activated macrophages and Kupffer cells and is 10 fold more potent than IL-12 in driving the development of Th1 cytokine synthesis in naïve and memory T cells. IL-18 synergizes with IL-12 in inducing IFN-γ production, in inhibiting IgE production in B cells, and in promoting the differentiation of CD8+ T cells and possibly CD8+ γδ cells, which have been shown to inhibit airway hyperreactivity. Production of both IL-12 and IL-18 may be enhanced by the presence of CpG ISS motifs in *Listeria* DNA, which can induce IL-12 and IL-18. However, it is unlikely that all the effects of HKL are due to CpG ISS, since HKL was much more effective than killed *Mycobacteria*, which also contain CpG ISS. Thus, the effectiveness of HKL as an adjuvant may therefore depend on the induction of IL-12, IL-18 and IFN-γ production, as well as the induction of CD8 and Th1 cells.

The mechanism by which HKL as an adjuvant reverses established airway hyperreactivity and inflammation may also involve the conversion of OVA-specific CD4+ Th2 cells into Th1 cells, or the inhibition or attrition of Th2 effector cells over time while a protective immune response develops from uncommitted OVA-specific precursor cells. Since the cytokine profile of Th2 effector cells are relatively fixed, the attrition of Th2 effector cells as well as the induction of several types of Th2-inhibiting regulatory cells may be involved in this process. Localization of antigen-specific Th1 cells in the lungs causes airway inflammation and lung injury, and does not reduce airway hyperreactivity and airway inflammation.

The attractiveness of *Listeria* as adjuvant therapy lies also in the fact that its immunomodulatory effects remain largely antigen specific. *Listeria* had minimal effect on airway hyperreactivity, IgE and cytokine production unless the *Listeria* was administered in a mixture with the antigen. Thus *Listeria* did not induce a generalized enhancement of IFN-γ production in recipients, but rather induced a protective response that was antigen-specific. The capacity to induce antigen-specific modulation is very important, because this specificity avoids non-specific immune augmentation, which could result in the development of autoimmune diseases. Antigen-specific therapy is feasible for the treatment of allergic rhinitis and allergic asthma, since the major offending allergens are virtually always identified. Thus, the use of *Listeria* as an adjuvant will greatly improve and refine conventional allergen immunotherapy (Creticos (1992) *JAMA* 268:2834–9), which currently requires multiple injections of soluble allergen over several years time, and is associated with frequent failures. The safety issues of using *Listeria* in humans is not of concern, since killed rather than live *Listeria* is effective for immune modulation.

In conclusion, it is demonstrated that allergen immunotherapy with HKL as adjuvant greatly inhibited the development of airway hyperreactivity and airway inflammation. Immunotherapy with HKL as adjuvant reversed ongoing airway disease, and converted allergic inflammatory responses into protective immune responses. The effect involved multiple mechanisms, including the induction of IL-18 and CD8+ T cells, activation of the innate immune system and inhibition of Th2 cytokine production.

INCORPORATION OF REFERENCES

All publications and patent applications cited in this specification are herein incorporated by reference as if each individual publication or patent application were specifically and individually indicated to be incorporated by reference.

OTHER EMBODIMENTS

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. It is particularly to be understood that the present invention is not limited to the particular embodiments described herein. For example, the invention is not restricted to the particular methodology, protocols, cell lines, animal species or genera, constructs and reagents described herein as such may vary. The foregoing has been merely a description of certain preferred embodiments of the invention, not intended to limit the scope of that invention, which is defined only by the appended claims.

What is claimed is:

1. A pharmaceutical composition for the treatment of allergies associated with an established allergen specific Th2-type T cell response, comprising:
   an allergen that causes Th2-type T cell response in a susceptible individual, *Listeria* adjuvant, and a pharmaceutically acceptable carrier; at a dose effective to convert said established Th2 type T cell response to a Th1 type immune response.

2. A pharmaceutical composition, comprising:
   an anaphylactic allergen, *Listeria* adjuvant, and a pharmaceutically acceptable carrier; at a dose effective to decrease an individual's hyperresponsiveness to the allergen.

3. The pharmaceutical composition of claim 1, wherein said allergen is associated with asthma.

4. The pharmaceutical composition of claim 1, wherein said allergen is a food allergen.

5. The pharmaceutical composition of claim 4, wherein said food is selected from the group consisting of nuts, milk protein, egg whites and shellfish.

6. The pharmaceutical composition of claim 1, wherein said allergen is an airborne allergen.

7. The pharmaceutical composition of claim 1, wherein said allergen is a drug allergen.

8. The pharmaceutical composition of claim 1, wherein said allergen is an insect venom.

9. The pharmaceutical composition of claim 2, wherein said allergen is a food allergen.

10. The pharmaceutical composition of claim 9, wherein said food is selected from the group consisting of nuts, milk protein, egg whites and shellfish.

11. The pharmaceutical composition of claim 2, wherein said allergen is an airborne allergen.

12. The pharmaceutical composition of claim 2, wherein said allergen is a drug allergen.

13. The pharmaceutical composition of claim 2, wherein said allergen is an insect venom.

14. A pharmaceutical composition for the treatment of allergies associated with an established allergen specific Th2-type T cell response, comprising:
   an allergen that causes Th2-type T cell response in a susceptible individual, *Listeria* adjuvant comprising heat killed *Listeria monocytogenes*, and a pharmaceutically acceptable carrier; at a dose effective to convert said established Th2 type T cell response to a Th1 type immune response.

* * * * *

UNITED STATES PATENT AND TRADEMARK OFFICE
CERTIFICATE OF CORRECTION

| | | |
|---|---|---|
| PATENT NO. | : 7,214,380 B1 | Page 1 of 1 |
| APPLICATION NO. | : 09/561089 | |
| DATED | : May 8, 2007 | |
| INVENTOR(S) | : DeKruyff et al. | |

It is certified that error appears in the above-identified patent and that said Letters Patent is hereby corrected as shown below:

Column 1:

• Please replace lines 14-17 with:

--This invention was made with Government support under contracts AI024571 and AI026322 awarded by the National Institutes of Health. The Government has certain rights in this invention.--

Signed and Sealed this
Nineteenth Day of April, 2011

David J. Kappos
*Director of the United States Patent and Trademark Office*